(12) United States Patent
Liverton et al.

(10) Patent No.: US 8,377,873 B2
(45) Date of Patent: Feb. 19, 2013

(54) HCV NS3 PROTEASE INHIBITORS

(75) Inventors: Nigel J. Liverton, Harleysville, PA (US); Vincenzo Summa, Rome (IT); Joseph P. Vacca, Telford, PA (US); Maria Emilia Di Francesco, Rome (IT); Marco Pompei, Rome (IT)

(73) Assignees: Merck Sharp & Dohme Corp., Rahway, NJ (US); Istituto di Ricerche di Biologia Molecolare P. Angeletti S.R.L., Rome (IT)

( * ) Notice: Subject to any disclaimer, the term of this patent is extended or adjusted under 35 U.S.C. 154(b) by 706 days.

(21) Appl. No.: 12/446,296

(22) PCT Filed: Oct. 19, 2007

(86) PCT No.: PCT/US2007/022344
§ 371 (c)(1),
(2), (4) Date: Apr. 20, 2009

(87) PCT Pub. No.: WO2008/051477
PCT Pub. Date: May 2, 2008

(65) Prior Publication Data
US 2010/0298210 A1   Nov. 25, 2010

Related U.S. Application Data

(60) Provisional application No. 60/853,837, filed on Oct. 24, 2006.

(51) Int. Cl.
*A61K 38/00* (2006.01)
*A01N 37/18* (2006.01)

(52) U.S. Cl. .................................... 514/3.7; 514/4.3

(58) Field of Classification Search .................. None
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,608,027 B1 | 8/2003 | Tsantrizos et al. | |
| 6,777,395 B2 | 8/2004 | Bhat et al. | |
| 6,955,174 B2 | 10/2005 | Friedrichs et al. | |
| 7,470,664 B2 | 12/2008 | Holloway et al. | |
| 2002/0019363 A1 | 2/2002 | Ismaili et al. | |
| 2002/0107138 A1 | 8/2002 | Hoveyda et al. | |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0229776 A1 | 11/2004 | Chen et al. | |
| 2004/0229818 A1 | 11/2004 | Llinas-Brunet | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0122123 A1* | 6/2006 | Chaudhary et al. ............. 514/18 |
| 2006/0257980 A1 | 11/2006 | Li | |
| 2007/0027071 A1 | 2/2007 | Holloway et al. | |

FOREIGN PATENT DOCUMENTS

| | | |
|---|---|---|
| EP | 1719773 A1 | 11/2006 |
| GB | 2337262 A | 11/1999 |
| GB | 2430621 A | 4/2007 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |

(Continued)

OTHER PUBLICATIONS

Brian W. Dymock et al., "Novel Approaches to the Treatment of Hepatitis C Virus Infection," 11 Antiviral Chemistry & Chemotherapy 79-96 (2000).

(Continued)

*Primary Examiner* — Thomas Heard
(74) *Attorney, Agent, or Firm* — Melissa B. Wenk; Sheldon O. Heber

(57) ABSTRACT

The present invention relates to macrocyclic compounds of formula (I) that are useful as inhibitors of the hepatitis C virus (HCV) NS3 protease, their synthesis, and their use treating or preventing HCV infections.

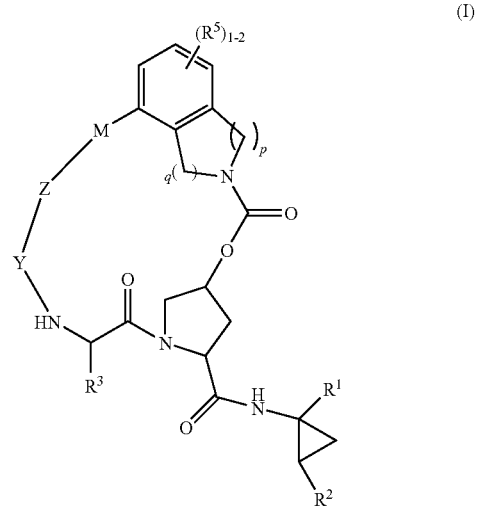

16 Claims, No Drawings

FOREIGN PATENT DOCUMENTS

| | | |
|---|---|---|
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A1 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Hugo R. Rosen & David R. Gretch, "Hepatitis C virus: current understanding and prospects for future therapies," 5 Molec. Med. Today 393-99 (1999).

Darius Moradpour & Hubert E Blum, "Current and evolving therapies for hepatitis C," 11 Euro. J. Gastroenterol. Hepatol. 1189-1202 (1999).

Ralf Bartenschlager, "Candidate Targets for Hepatitis C Virus-Specific Antiviral Therapy," 40(5-6) Intervirology 378-93 (1997).

Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Tmka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexan-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3¦4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Youwei Yan et al., Complex of NS3 protease and NS4A peptide of BK strain hepatitis C virus: A 2.2 Angstrom resolution structure in a hexagonal crystal form, 7 Protein Science 837 (1998).

* cited by examiner

HCV NS3 PROTEASE INHIBITORS

CROSS-REFERENCE TO RELATED APPLICATIONS

This application is a National Stage application of International Patent Application No. PCT/US2007/022344, filed Oct. 19, 2007. This application also claims priority to U.S. Provisional Patent Application No. 60/853,837, filed Oct. 24, 2006.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: B. Dymock, et al., "Novel approaches to the treatment of hepatitis C virus infection," *Antiviral Chemistry & Chemotherapy*, 11: 79-96 (2000); H. Rosen, et al., "Hepatitis C virus: current understanding and prospects for future therapies," *Molecular Medicine Today*, 5: 393-399 (1999); D. Moradpour, et al., "Current and evolving therapies for hepatitis C," *European J. Gastroenterol. Hepatol.*, 11: 1189-1202 (1999); R. Bartenschlager, "Candidate Targets for Hepatitis C Virus-Specific Antiviral Therapy," *Intervirology*, 40: 378-393 (1997); G. M. Lauer and B. D. Walker, "Hepatitis C Virus Infection," *N. Engl. J. Med.*, 345: 41-52 (2001); B.W. Dymock, "Emerging therapies for hepatitis C virus infection," *Emerging Drugs*, 6: 13-42 (2001); and C. Crabb, "Hard-Won Advances Spark Excitement about Hepatitis C," *Science:* 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. Previous research has identified classes of peptides, such as hexapeptides as well as tripeptides discussed in U.S. patent applications US2005/0020503, US2004/0229818, and US2004/00229776, showing degrees of activity in inhibiting the NS3 protease. The aim of the present invention is to provide further compounds which exhibit activity against the HCV NS3 protease.

SUMMARY OF THE INVENTION

The present invention relates to novel macrocyclic compounds of formula (I) and/or pharmaceutically acceptable salts or hydrates thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts or hydrates (when appropriate), or as pharmaceutical composition ingredients, whether or not in combination with other HCV antivirals, anti-infectives, immunomodulators, antibiotics or vaccines. More particularly, the present invention relates to a compound of formula (I) and/or a pharmaceutically acceptable salt or hydrate thereof:

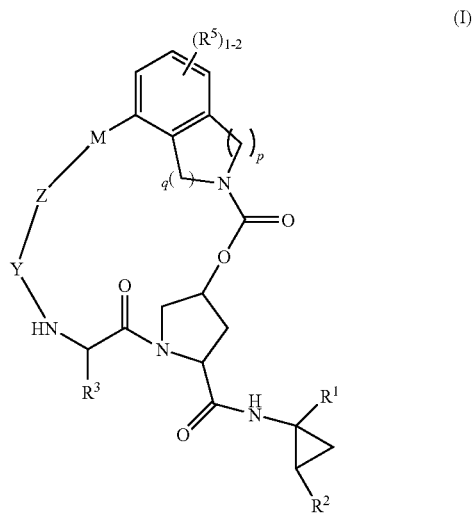

wherein:

p and q are independently 1 or 2;

$R^1$ is —CONHR$^6$, —CONHP(O)R$^{11}$R$^{12}$, or —P(O)R$^{11}$R$^{12}$, and $R^2$ is $C_1$-$C_6$ alkyl, $C_2$-$C_6$ alkenyl or $C_3$-$C_8$ cycloalkyl, wherein said alkyl, alkenyl or cycloalkyl is optionally substituted with 1 to 3 halo, or $R^1$ and $R^2$, together with the cyclopropyl ring to which they are attached, form the following bicyclic ring system:

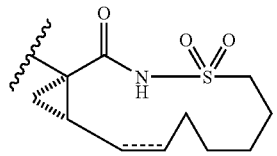

wherein ===== is a single or double bond;

$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —NHCOOR$^6$, —NHCOR$^6$, —NHCONHR$^6$, —$CO_2R^{10}$, —$C(O)R^{10}$, and —$CON(R^{10})_2$;

Het is a 5- to 6-membered saturated cyclic ring having 1 or 2 heteroatoms selected from N, O and S, wherein said ring is optionally substituted with 1 to 3 substituents selected from halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —NHCOOR$^6$, —NHCOR$^6$, —NHCONHR$^6$, —$CO_2R^{10}$, —$C(O)R^{10}$, and —$CON(R^{10})_2$;

$R^4$ is H, $C_1$-$C_8$ alkyl, $C_3$-$C_8$ cycloalkyl($C_1$-$C_8$)alkyl, or aryl($C_1$-$C_8$)alkyl; wherein aryl is phenyl or naphthyl and said alkyl, cycloalkyl, or aryl is optionally substituted with 1 to 3 substituents selected from the group consisting of halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —NHCOOR$^6$, —NHCOR$^6$, —NHCONHR$^6$, —$CO_2R^{10}$, —$C(O)R^{10}$, and —$CON(R^{10})_2$;

$R^5$ is H, halo, —$OR^{10}$, $C_1$-$C_6$ alkyl, —CN, —$CF_3$, —$SR^{10}$, —$SO_2(C_1$-$C_6$ alkyl), $C_3$-$C_8$ cycloalkyl, $C_3$-$C_8$ cycloalkoxy, $C_1$-$C_6$ haloalkyl, —$N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), NHCOOR$^6$, NHCOR$^6$, NHCONHR$^6$, $CO_2R^{10}$, $C(O)R^{10}$, and)$CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^6$ is $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents or aryl is substituted by P(O)$R^{11}R^{12}$; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is —C(=O)—, —$SO_2$—, or —C(=N—CN)—;

Z is —$C(R^{10})_2$—, —O—, or —$N(R^4)$—;

M is $C_1$-$C_{12}$ alkylene or $C_2$-$C_{12}$ alkenylene, wherein said alkylene or alkenylene is optionally substituted with 1 or 2 substituents selected from the group consisting of $C_1$-$C_8$ alkyl, $C_3$-$C_8$ cycloalkyl($C_1$-$C_8$ alkyl), and aryl($C_1$-$C_8$ alkyl); and the 2 adjacent substituents of M are optionally taken together to form a 3- to 6-membered cyclic ring containing 0-3 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, —$OR^{10}$, $C_1$-$C_6$ alkyl, —CN, —$CF_3$, —$NO_2$, —$SR^{10}$, —$CO_2R^{10}$, —$CON(R^{10})_2$, —$C(O)R^{10}$, —$N(R^{10})C(O)R^{10}$, —$SO_2(C_1$-$C_6$ alkyl), —$S(O)(C_1$-$C_6$alkyl), $C_3$-$C_8$ cycloalkyl, $C_3$-$C_8$ cycloalkoxy, $C_1$-$C_6$ haloalkyl, —$N(R^{10})_2$, —$N(C_1$-$C_6$ alkyl)$O(C_1$-$C_6$ alkyl), halo($C_1$-$C_6$ alkoxy), —$NR^{10}SO_2R^{10}$, —$SO_2N(R^{10})_2$, —NHCOOR$^{10}$, —NHCONHR$^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

each $R^{10}$ is independently H or $C_1$-$C_6$ alkyl;

each $R^{11}$ is independently $C_1$-$C_6$ alkyl, $C_1$-$C_4$ alkenyl, —$OR^{13}$), —$N(R^{10})$—V—$CO_2R^{10}$, —O—V—$CO_2R^{10}$, —S—V—$CO_2R^{10}$, —$N(R^{10})(R^{13})$, $R^{14}$, or —$N(R^{10}SO_2R^6$;

each $R^{12}$ is independently —$OR^{13}$, —$N(R^{10})$—V—$CO_2R^{10}$, —O—V—$CO_2R^{10}$, —S—V—$CO_2R^{10}$, or —$N(R^{10})(R^{13})$;

or $R^{11}$ and $R^{12}$ are optionally taken together, with the phosphorus atom to which they are attached, to form a 5- to 7-membered monocyclic ring;

each V is independently —$CH(R^{15})$ or $C_1$-$C_4$ alkylene-CH($R^{15}$);

each $R^{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, —OC(O)OR$^6$, —OC(O)R$^6$, —$OR^{10}$, —$SR^{10}$, —$N(R^{10})_2$, —$C(O)R^{10}$, —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —NHCOOR$^6$, —NHCOR$^6$, —NHCONHR$^6$, —$CO_2R^{10}$, and —$C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of $C_1$-$C_6$ alkyl, halo, —OC(O)OR$^6$, —OC(O)R$^6$, —OR$^{10}$, —SR$^{10}$, —N(R$^{10}$)$_2$, —C(O)R$^{10}$, —NO$_2$, —CN, —CF$_3$, —SO$_2$($C_1$-$C_6$ alkyl), —S(O)($C_1$-$C_6$ alkyl), —S(O)($C_1$-$C_6$alkyl), —NR$^{10}$SO$_2$R$^6$, —SO$_2$R$^6$, —SO$_2$N(R$^6$)$_2$, —NHCOOR$^6$, —NHCOR$^6$, —NHCONHR$^6$, —CO$_2$R$^{10}$, and —C(O)N(R$^{10}$)$_2$; and each $R^{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of $C_1$-$C_6$ alkyl, halo, —OC(O)OR$^6$, —OC(O)R$^6$, —OR$^{10}$, —SR$^{10}$, —N(R$^{10}$)$_2$, —C(O)R$^{10}$, —NO$_2$, —CN, —CF$_3$, —SO$_2$($C_1$-$C_6$ alkyl), —S(O)($C_1$-$C_6$ alkyl), —NR$^{10}$SO$_2$R$^6$, —SO$_2$N(R$^6$)$_2$, —NHCOOR$^6$, —NHCOR$^6$, —NHCONHR$^6$, —CO$_2$R$^{10}$, and —C(O)N(R$^{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

In one embodiment of the invention, p and q are 1, and all other variables are as previously defined.

In another embodiment of the invention, $R^1$ is —P(O)R$^{11}$R$^{12}$, and all other variables are as previously defined. In a preferred group of this embodiment, $R^{11}$ is independently $C_1$-$C_6$ alkyl, $C_1$-$C_4$alkenyl, or —OR$^{13}$, and $R^{12}$ is independently —OR$^{13}$, and all other variables are as previously defined. In a more preferred group of this embodiment, $R^{13}$ is H or $C_1$-$C_6$ alkyl, and all other variables are as previously defined. In an even more preferred embodiment of the invention, $R^{11}$ is selected from the group consisting of —OCH$_2$CH$_3$, —CH$_2$CH$_3$, —CH$_3$, —CH(CH$_3$)$_2$, phenyl, —CH=CH$_2$, OH, —CH$_2$CH$_2$CH$_3$, and —CH$_2$CH$_2$CH$_2$CH$_3$, and $R^{12}$ is —OH or —OCH$_2$CH$_3$, and all other variables are as previously defined.

In another embodiment of the invention, $R^2$ is $C_1$-$C_6$ alkyl or $C_2$-$C_6$ alkenyl, and all other variables are as previously defined. In a more preferred group of this embodiment, $R^2$ is —CH=CH$_2$ or —CH$_2$CH$_3$, and all other variables are as previously defined.

In another embodiment of the invention, $R^1$ and $R^2$, together with the cyclopropyl ring to which they are attached, form the following bicyclic ring system:

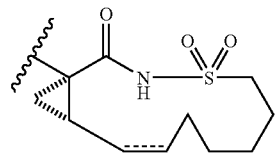

wherein ===== is a single or double bond, and all other variables are as previously defined.

In another embodiment of the invention, $R^3$ is $C_1$-$C_8$ alkyl or $C_3$-$C_8$ cycloalkyl, and all other variables are as previously defined. In a preferred group of this embodiment, $R^3$ is —C(CH$_3$)$_3$, cyclohexyl or cyclopentyl, and all other variables are as previously defined.

In another embodiment of the invention, $R^5$ is H, and all other variables are as previously defined.

In another embodiment of the invention, Z is —O—, and all other variables are as previously defined.

In another embodiment of the invention, Y is —C(=O)—, and all other variables are as previously defined.

In another embodiment of the invention, M is $C_1$-$C_{12}$ alkylene or $C_2$-$C_{12}$ alkenylene, wherein said alkylene or alkenylene is optionally substituted with 1 or 2 substituents selected from the group consisting of $C_1$-$C_8$ alkyl, and all other variables are as previously defined. In a preferred group of this embodiment, M is selected from the group consisting of —(CH$_2$)$_4$C(CH$_3$)$_2$(CH$_2$)—, —(CH$_2$)$_6$—, —(CH$_2$)$_4$CH(CH$_3$)CH$_2$—, —CH=CH(CH$_2$)$_2$C(CH$_3$)$_2$CH$_2$—, —CH=CH(CH$^2$)$_2$CH(CH$_3$)CH$_2$—, —CH=CHCH$_2$C(CH$_3$)$_2$CH$_2$—, —CH=CH(CH$_2$)$_3$—, —CH=CH(CH$_2$)$_4$, —CH=CHCH$_2$CH(CH$_3$)CH$_2$—, —(CH$_2$)$_3$C(CH$_3$)$_2$CH$_2$—, —(CH$_2$)$_5$—, and —(CH$_2$)$_3$CH(CH$_3$)CH$_2$—, and all other variables are as previously defined.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts and/or hydrates thereof. These compounds and their pharmaceutically acceptable salts and/or hydrates are HCV protease inhibitors (e.g., HCV NS3 protease inhibitors). The present invention also includes compounds of formulae II, II-a, II-b, II-c, II-d, III, III-a, III-b, III-c, and III-d wherein all variables are as defined for formula I.

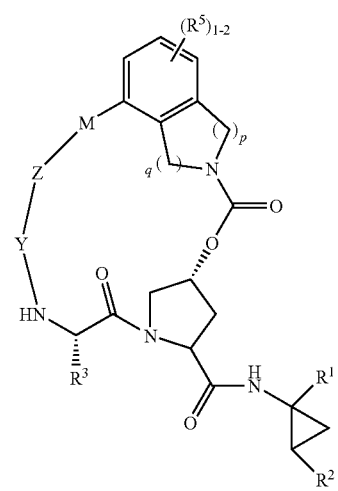

II-a
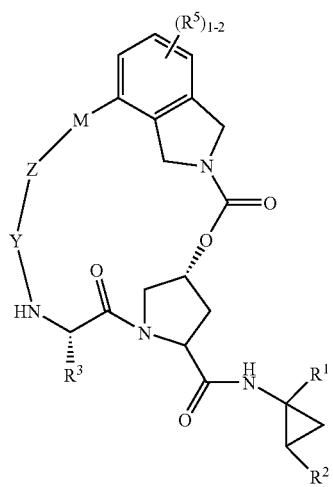
II-d
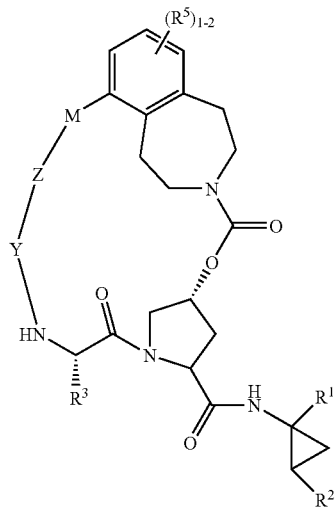
II-b
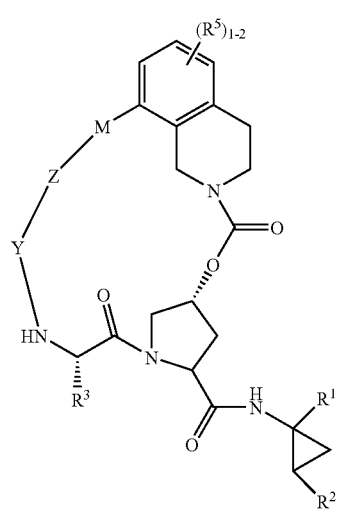
III
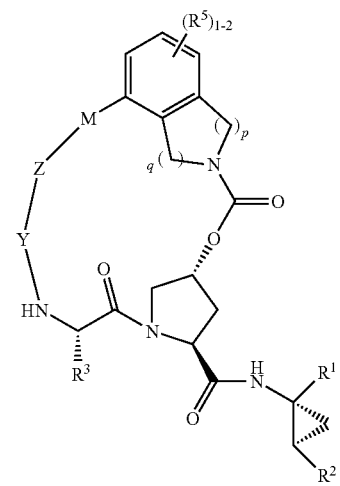
II-c
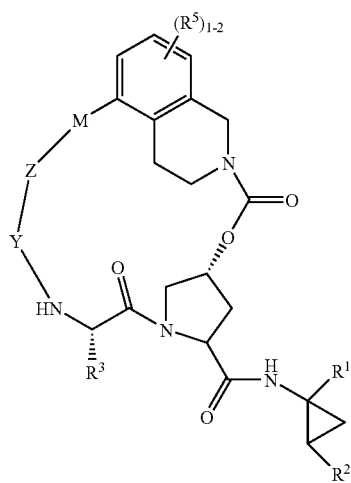
III-a
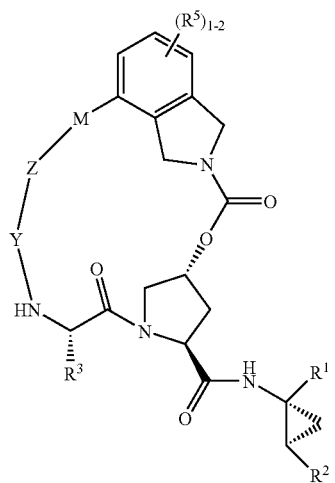

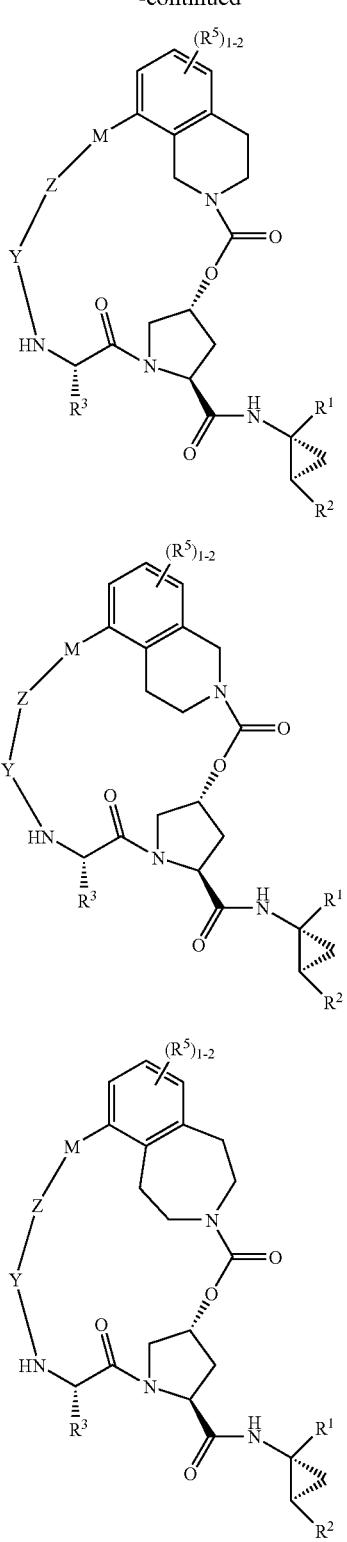

Other embodiments of the present invention include the following:

(a) A pharmaceutical composition comprising an effective amount of a compound of formula I, II, II-a, II-b, II-c, II-d, III, III-a, III-b, III-c, or III-d and a pharmaceutically acceptable carrier.

(b) The pharmaceutical composition of (a), further comprising a second therapeutic agent selected from the group consisting of a HCV antiviral agent, an immunomodulator, and an anti-infective agent.

(c) The pharmaceutical composition of (b), wherein the HCV antiviral agent is an antiviral selected from the group consisting of a HCV protease inhibitor and a HCV NS5B polymerase inhibitor.

(d) A pharmaceutical combination which is (i) a compound of formula I, II, II-a, II-b, II-c, II-d, III, III-a, III-b, III-c, or III-d and (ii) a second therapeutic agent selected from the group consisting of a HCV antiviral agent, an immunomodulator, and an anti-infective agent; wherein the compound of formula I, II, II-a, II-b, II-c, II-d, III, III-a, III-b, III-c, or III-d and the second therapeutic agent are each employed in an amount that renders the combination effective for inhibiting HCV NS3 protease, or for treating or preventing infection by HCV.

(e) The combination of (d), wherein the HCV antiviral agent is an antiviral selected from the group consisting of a HCV protease inhibitor and a HCV NS5B polymerase inhibitor.

(f) A method of inhibiting HCV NS3 protease in a subject in need thereof which comprises administering to the subject an effective amount of a compound of formula I, II, II-a, II-b, II-c, II-d, III, III-a, III-b, III-c, or III-d.

(g) A method of preventing or treating infection by HCV in a subject in need thereof which comprises administering to the subject an effective amount of a compound of formula I, II, II-a, II-b, II-c, II-d, III, III-a, III-b, III-c, or III-d.

(h) The method of (g), wherein the compound of formula I, II, II-a, II-b, II-c, II-d, III, III-a, III-b, III-c, or III-d is administered in combination with an effective amount of at least one second therapeutic agent selected from the group consisting of a HCV antiviral agent, an immunomodulator, and an anti-infective agent.

(i) The method of (h), wherein the HCV antiviral agent is an antiviral selected from the group consisting of a HCV protease inhibitor and a HCV NS5B polymerase inhibitor.

(j) A method of inhibiting HCV NS3 protease in a subject in need thereof which comprises administering to the subject the pharmaceutical composition of (a), (b), or (c) or the combination of (d) or (e).

(k) A method of preventing or treating infection by HCV in a subject in need thereof which comprises administering to the subject the pharmaceutical composition of (a), (b), or (c) or the combination of (d) or (e).

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

The present invention also includes a compound of the present invention for use (i) in, (ii) as a medicament for, or (iii) in the preparation of a medicament for: (a) inhibiting HCV NS3 protease, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, the term "alkyl" refers to any linear or branched chain alkyl group having a number of carbon atoms in the specified range. Thus, for example, "$C_6$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "haloalkyl" refers to an alkyl group wherein a hydrogen has been replaced by a halogen. The term "alkoxy" refers to an "alkyl-O—" group.

The term "alkylene" refers to any linear or branched chain alkylene group (or alternatively "alkanediyl") having a number of carbon atoms in the specified range. Thus, for example, "—$C_6$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The terms "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group.

The term "halogen" (or "halo") refers to fluorine, chlorine, bromine and iodine (alternatively referred to as fluoro, chloro, bromo, and iodo).

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g., $R^7$ and $R^{10}$) occurs more than one time in any constituent or in formula I, II, II-a, II-b, II-c, II-d, III, III-a, III-b, III-c, or III-d or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula I, II, II-a, II-b, II-c, II-d, III, III-a, III-b, or III-d is a reference to the compound per se, or to any one of its tautomers per se, or to mixtures of two or more tautomers.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and preventing or treating HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), ALBUFERON (interferon-α bound to human serum albumin (Human Genome Sciences)), and a purified interferon-α product. Amgen's recombinant consensus interferon has the brand name INFERGEN®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil (see A. C. Allison and E. M. Eugui, *Agents Action,* 44 (Suppl.): 165 (1993)).

For the treatment of HCV infection, the compounds of the present invention may also be administered in combination with the antiviral agent amantadine (1-aminoadamantane) [for a comprehensive description of this agent, see J. Kirschbaum, Anal. Profiles Drug Subs. 12: 1-36 (1983)]. For the treatment of HCV infection, the compounds of the present invention may also be administered in combination with the antiviral agent polymerase inhibitor R7128 (Roche).

The compounds of the present invention may also be combined for the treatment of HCV infection with antiviral 2'-C-branched ribonucleosides disclosed in R. E. Harry-O'Kuru, et al., *J. Org. Chem.,* 62: 1754-1759 (1997); M. S. Wolfe, et al., *Tetrahedron Lett.,* 36: 7611-7614 (1995); U.S. Pat. No. 3,480, 613 (Nov. 25, 1969); International Publication Number WO 01/90121 (29 Nov. 2001); International Publication Number WO 01/92282 (6 Dec. 2001); and International Publication Number WO 02/32920 (25 Apr. 2002); and International Publication Number WO 04/002999 (8 Jan. 2004); and International Publication Number WO 04/003000 (8 Jan. 2004); and International Publication Number WO 04/002422 (8 Jan. 2004); the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO 02/32920, WO 02/48165 (20 Jun. 2002), and WO2005003147 (13 Jan. 2005) (including R1656, (2'R)-2'-deoxy-2'-fluoro-2'-C-methylcytidine, shown as compounds 3-6 on page 77) assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), US2005/0038240 (Feb. 17, 2005) and WO2006021341 (2 Mar. 2006), including 4'-azido nucleosides such as R1626, 4'-azidocytidine, assigned to Hoffmann-LaRoche; U.S. 2002/0019363 (14 Feb. 2002); WO 02/100415 (19 Dec. 2002); WO 03/026589 (3 Apr. 2003); WO 03/026675 (3 Apr. 2003); WO 03/093290 (13 Nov. 2003); US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004); the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in WO 02/057287, U.S. Pat. No. 6,777,395, WO 02/057425, US 2004/0067901, WO 03/068244, WO 2004/000858, WO 04/003138 and WO 2004/007512; the content of each is incorporated herein by reference in its entirety. Other such HCV polymerase inhibitors include, but are not limited to, valopicitabine (NM-283; Idenix) and 2'-F-2'-beta-methyl-cytidine (see also WO 2005/003147, assigned to Pharmasset, Ltd.).

In one embodiment, nucleoside HCV NS5B polymerase inhibitors that are used in combination with the present HCV NS3 protease inhibitors are selected from the following compounds:
4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; WO 02/20497 (3 Mar. 2002); WO 2005/016927 (in particular JTK003), assigned to Japan Tobacco, Inc.; the content of each of these references is incorporated herein by reference in its entirety; and HCV-796 (Viropharma Inc.).

The HCV NS3 protease inhibitory activity of the present compounds may be tested using assays known in the art. One such assay is HCV NS3 protease time-resolved fluorescence (TRF) assay as described below and in WO2006/102087.Other examples of such assays are described in e.g., International Patent Publication WO2005/046712. Compounds useful as HCV NS3 protease inhibitors would have a Ki less than 50 μM, more preferably less than 10 μM, and even more preferably less than 100 nM.

The present invention also includes processes for making compounds of formula I, II, II-a, II-b, II-c, II-d, III, III-a, III-b, III-c, or III-d. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice. The examples are not to be construed as limitations on the scope or spirit of the invention.

General Description of Synthesis:

The compounds of the present invention may be synthesized as outlined in the general Schemes 1 and 2.

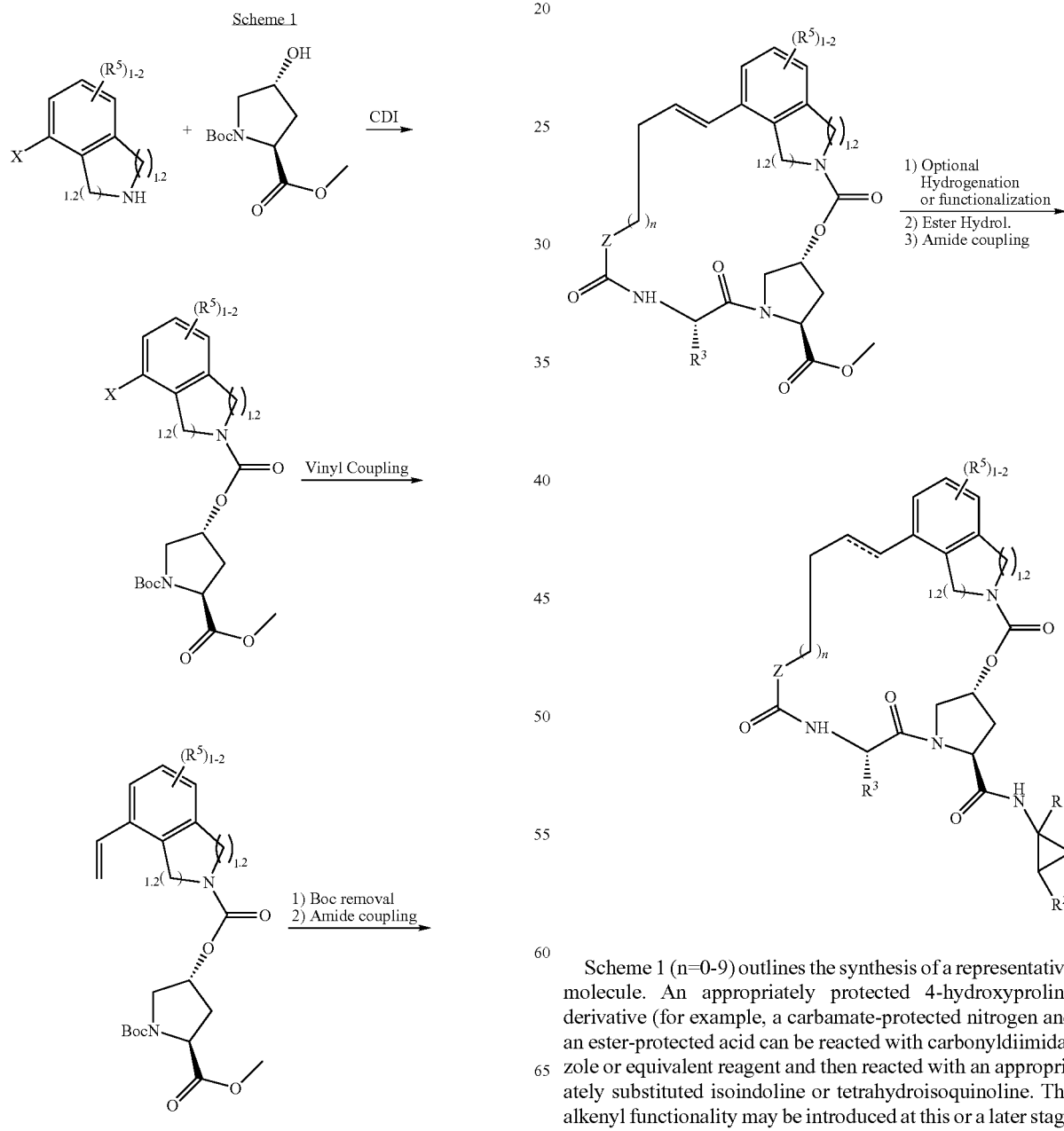

Scheme 1 (n=0-9) outlines the synthesis of a representative molecule. An appropriately protected 4-hydroxyproline derivative (for example, a carbamate-protected nitrogen and an ester-protected acid can be reacted with carbonyldiimidazole or equivalent reagent and then reacted with an appropriately substituted isoindoline or tetrahydroisoquinoline. The alkenyl functionality may be introduced at this or a later stage by palladium-catalyzed reaction of a halide substituent such as chloride, bromide and iodide, or other functionality such as a triflate with an organometallic reagent such as a vinyl or allyltrialkyltin. Alternatively, the alkenyl functionality may be introduced prior to the reaction with protected prolinol.

skilled in the art (Theodora W. Greene, *Protective Groups in Organic Synthesis*, Third Edition, John Wiley and Sons, 1999).

Deprotection of the carbamate protecting group on the proline portion may be carried out by a variety of methods Scheme 2

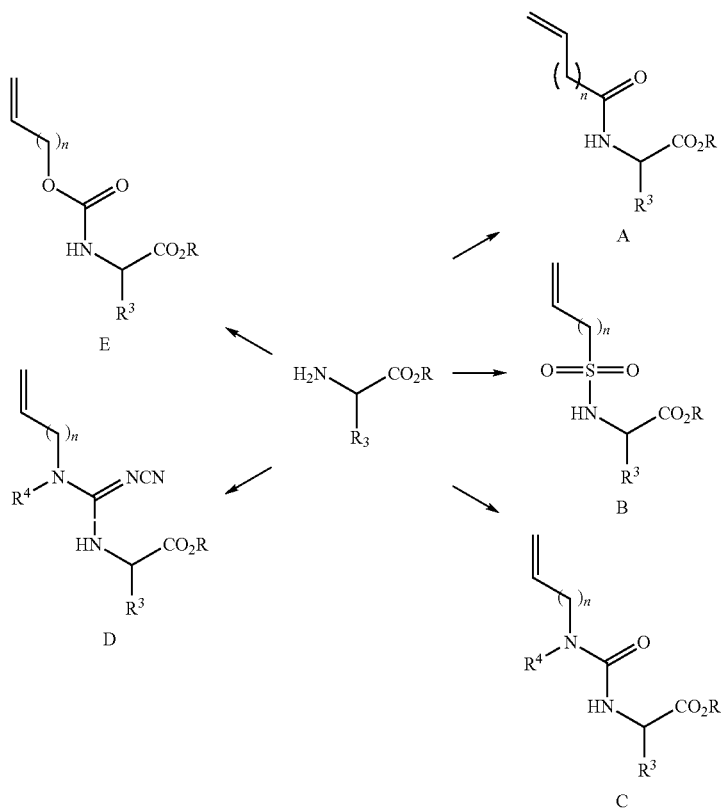

Scheme 2 describes the synthesis of the olefin containing amino acid portion. An amino acid (either commercially available or may be prepared readily using known methods in the art) in which the acid functionality is protected as an ester (for example, R=methyl) can be converted to amides A by coupling an olefinic carboxylic acid utilizing a wide range of peptide coupling agents known to those skilled in the art such as DCC, EDC, BOP, TBTU, etc. Preparation of the Sulfonamides B can be Accomplished by Reaction with the Appropriate Sulfonyl chloride in an organic solvent (e.g., THF) with an amine base as scavenger. Urea derivatives C may be prepared by reacting the aminoester with a reagent such as carbonyldiimidazole, to form an intermediate isocyanate (Catalano et al., WO 03/062192) followed by addition of a second olefin-containing amine. Alternatively, phosgene, diphosgene or triphosgene may be used in place of carbonyldiimidazole. Cyanoguanidine derivatives D can be prepared by reaction of the amino acid ester with diphenyl C-cyanocarbonimidate in an organic solvent, followed by addition of a second olefin-containing amine. Carbamate derivatives E may be prepared by reacting an olefin-containing alcohol with carbonyldiimidazole (or phosgene, triphosgene or diphosgene) in an organic solvent, followed by addition of the amino ester.

Following functionalization of the amine, the ester can be hydrolyzed under a range of basic conditions known to those known to persons skilled in the art (Theodora W. Greene, *Protective Groups in Organic Synthesis*, Third Edition, John Wiley and Sons, 1999).

To complete the synthesis of the compounds of this invention, the amino acid derivative can be coupled to the proline derivative via a wide range of peptide coupling reagents such as DCC, EDC, BOP, TBTU etc (see Scheme 1). Macrocyclization is then achieved by an olefin metathesis using a range of catalysts that have been described in the literature for this purpose. At this stage, the olefinic bond produced in the ring-closing metathesis may be optionally hydrogenated to give a saturated linkage or functionalized in alternative ways such as cyclopropanation. The proline ester is then hydrolyzed under basic conditions and coupled with an appropriate cyclopropyl containing P1 fragment, the syntheses of which have been described previously (Llinas-Brunet et al., U.S. Pat. No. 6,323,180; Chaudhary, WO2006/020276) and subjected to an additional hydrolysis step to provide the final compounds.

Olefin metathesis catalysts include the following Ruthenium based species: F: Miller et al *J. Am. Chem. Soc* 1996, 118, 9606; G: Kingsbury et al *J. Am. Chem. Soc* 1999, 121, 791; H: Scholl et al Org. Lett. 1999, 1, 953; Hoveyda et al US2002/0107138; K: Furstner et al. J. Org. Chem. 1999, 64, 8275. The utility of these catalysts in ring-closing metathesis is well known in the literature (e.g. Trnka and Grubbs, *Acc. Chem. Res.* 2001, 34, 18).

F

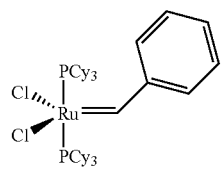

G

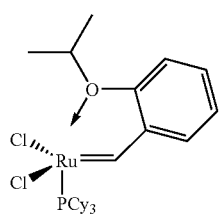

H

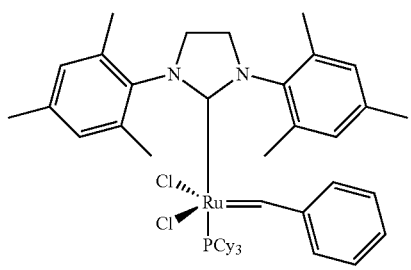

J

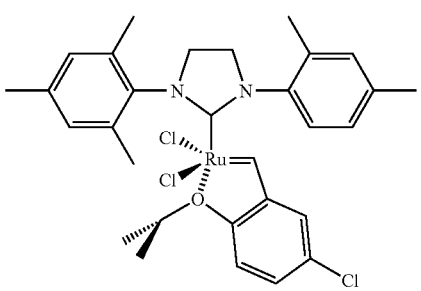

K

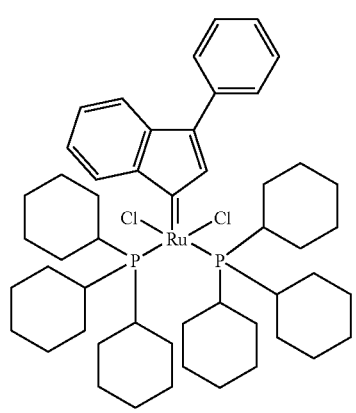

L

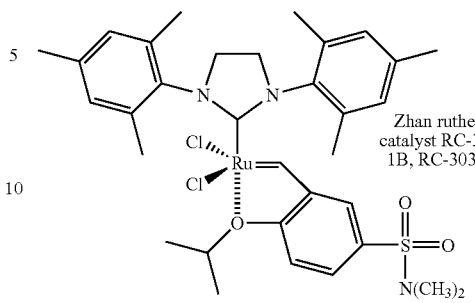

Zhan ruthenium metathesis catalyst RC-303 (Zhan catalyst 1B, RC-303, Zannan Pharma Ltd.)

LIST OF ABBREVIATIONS

| | | |
|---|---|---|
| | BOP | Benzotriazole-1-yl-oxy-tris-(dimethylamino)-phosphonium hexafluorophosphate |
| | $CH_3CN$ | Acetonitrile |
| | DBU | 1,8-Diazabicyclo[5.4.0]undec-7-ene |
| | DCC | Dicyclohexylcarbodiimide |
| | DCE | Dichloroethane |
| | DCM | Dichloromethane |
| | DIPEA | Diisoproylethylamine |
| | DMAP | 4-Dimethylamino pyridine |
| | DMF | Dimethylformamide |
| | DMSO | Dimethyl sulfoxide |
| | EDC | N-(3-Dimethylaminopropyl)-N'-ethylcarbodiimide |
| | $Et_3N$ | Triethylamine |
| | $Et_2O$ | Diethyl ether |
| | EtOAc | Ethyl acetate |
| | EtOH | Ethanol |
| | HATU | O-(7-Azabenzotriazol-1-yl)-N,N,N',N'-tetramethyluronium hexafluorophosphate |
| | HBr | Hydrobromic acid |
| | HCl | Hydrochloric acid |
| | HOAc | Acetic acid |
| | HOAt | 1-Hydroxy-7-azabenzotriazole |
| | LiOH | Lithium hydroxide |
| | MeOH | Methanol |
| | $MgSO_4$ | Magnesium Sulfate |
| | MTBE | Methyl t-butyl ether |
| | $Na_2SO_4$ | Sodium sulfate |
| | $NaHCO_3$ | Sodium bicarbonate |
| | NaOH | Sodium hydroxide |
| | $NH_4Cl$ | Ammonium chloride |
| | $NH_4OH$ | Ammonium hydroxide |
| | Pd/C | Palladium on carbon |
| | $Pd(PPh_3)_4$ | Tetrakis(triphenylphosphine)palladium (0) |
| | PhMe | Toluene |
| | $PPh_3$ | Triphenylphosphine |
| | RT | Room temperature |
| | TBTU | O-Benzotriazol-1-yl-N,N,N',N'-tetramethyluronium tetrafluoroborate |
| | THF | Tetrahydrofuran |

Synthesis of Intermediates

Intermediates A

| Intermediate # | Structure | Name | Lit. Reference |
|---|---|---|---|
| A1 | 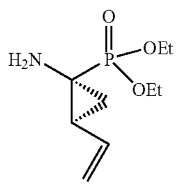 | diethyl [(1S,2R)-1-amino-2-vinylcyclopropyl]phosphonate | Chaudhary WO2006/020276 |
| A2 | 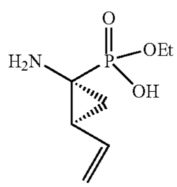 | ethyl hydrogen [(1S,2R)-1-amino-2-vinylcyclopropyl]phosphonate | Chaudhary WO2006/020276 |
| A3 | 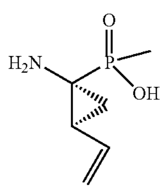 | [(1S,2R)-1-amino-2-vinylcyclopropyl]methylphosphinic acid | Chaudhary WO2006/020276 |
| A4 | 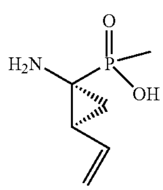 | [(1S,2R)-1-amino-2-vinylcyclopropyl]ethylphosphinic acid | Chaudhary WO2006/020276 |
| A5 | 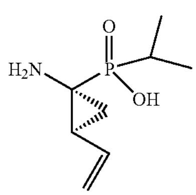 | [(1S,2R)-1-amino-2-vinylcyclopropyl]isopropylphosphinic acid | Chaudhary WO2006/020276 |
| A6 | 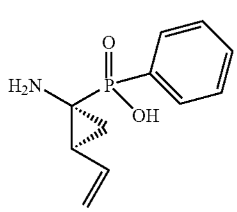 | [(1S,2R)-1-amino-2-vinylcyclopropyl]phenylphosphinic acid | Chaudhary WO2006/020276 |
| A7 | 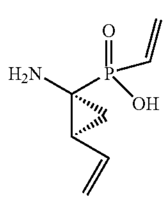 | [(1S,2R)-1-amino-2-vinylcyclopropyl]vinylphosphinic acid | Chaudhary WO2006/020276 |

-continued

| Intermediate # | Structure | Name | Lit. Reference |
|---|---|---|---|
| A8 | 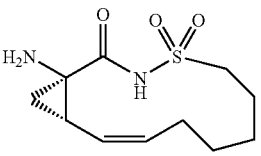 | 1-amino-4-thia-3-azabicyclo[10.1.0]tridec-10-en-2-one 4,4-dioxide | Chaudhary WO2006/020276 |
| A9 | 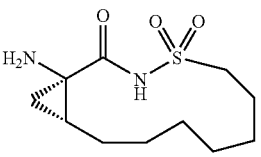 | 1-amino-4-thia-3-azabicyclo[10.1.0]tridecan-2-one 4,4-dioxide | Chaudhary WO2006/020276 |

By hydrogenation of the intermediates above, or a suitable intermediate in their preparation, for example by treatment in an appropriate solvent or solvent mixture with a palladium, platinum or rhodium catalyst, the following intermediates can be prepared by a person skilled in the art.

| Intermediate # | Structure | Name |
|---|---|---|
| A10 | 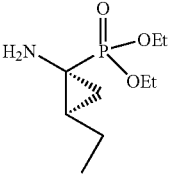 | diethyl [(1S,2S)-1-amino-2-ethylcyclopropyl]phosphonate |
| A11 | 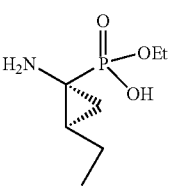 | ethyl hydrogen [(1S,2S)-1-amino-2-ethylcyclopropyl]phosphonate |
| A12 | 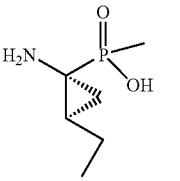 | [(1S,2S)-1-amino-2-ethylcyclopropyl]methylphosphinic acid |
| A13 | 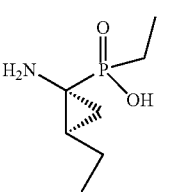 | [(1S,2S)-1-amino-2-ethylcyclopropyl]ethylphosphinic acid |
| A14 | 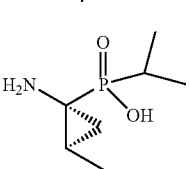 | [(1S,2S)-1-amino-2-ethylcyclopropyl]isopropylphosphinic acid |

-continued

| Intermediate # | Structure | Name |
|---|---|---|
| A15 | 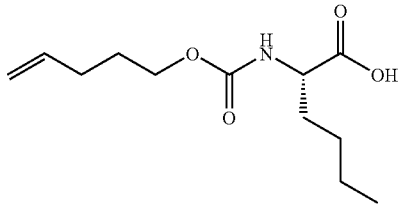 [SMILES: C=CCCCOC(=O)N[C@@H](CCCC)C(=O)O] | [(1S,2S)-1-amino-2-ethylcyclopropyl]phenylphosphinic acid |

Intermediates B

Intermediate B1:
N-[(pent-4-en-1-yloxy)carbonyl]-norleucine

To a solution of 1-penten-4-ol (0.95 g, 11.0 mmol) in DMF (15 mL) at 0° C. was added carbonyldiimidazole (1.79 g, 11.0 mmol). The reaction mixture was warmed to RT and stirred for 30 minutes. L-norleucine methyl ester hydrochloride (2.0 g, 11.0 mmol) was then added, the reaction mixture was heated to 50° C. and stirred for 15 minutes. Upon cooling, the reaction mixture was diluted with ethyl ether and washed twice with water. The organic layer was dried over Na$_2$SO$_4$, filtered and concentrated. The crude product was purified by silica gel chromatography (gradient elution 10 to 90% EtOAc in hexanes) to afford 2.1 g (74%) methyl N-[(pent-4-en-1-yloxy)carbonyl]-L-norleucinate as a clear oil.

To a stirred solution of methyl N-[(pent-4-enyloxy)carbonyl]-norleucinate (8.50 g, 33.03 mmol) in THF (20 mL) was added 1 N NaOH (20 mL). This reaction solution was stirred at RT for 3 hours, then acidified to pH 3 with 1 N HCl and extracted with (3×250 mL) EtOAc. The combined EtOAc layer was washed with 50 mL water, 50 mL brine, dried over Na$_2$SO$_4$, filtered and concentrated to give 7.09 g (88%) of the title product as clear oil. LRMS (ESI) m/z 244 [(M+H)$^+$; calcd for C$_{12}$H$_{22}$NO$_4$: 244].

Intermediate B2: (2S)-3,3-dimethyl-2-{[(pent-4-en-1-yloxy)carbonyl]amino}butanoic acid

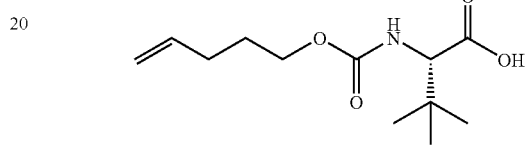

Diisopropylethyl amine (9.85 g, 76.2 mmol) was added dropwise to a 0° C. solution of 4-penten-1-ol (7.22 g, 83.9 mmol) and triphosgene (11.3 g, 38.1 mmol) in 160 mL dioxane. The resulting white suspension was stirred for 5 minutes at 0° C., then allowed to warm to 25° C. over 1 hour. The suspension was cooled to 0° C. with an ice bath and 1 N NaOH (76.2 mL) and L-t-butylglycine (10.0 g, 76.2 mmol) were added. The reaction mixture was warmed to 25° C. and stirred for 18 hours. The dioxane was removed in vacuo and the reaction mixture was basified to pH 12 with 1 N NaOH. The aqueous layer was extracted with DCM (3×150 mL), then acidified to pH~1 with 6 N HCl. The aqueous layer was extracted with DCM (3×150 mL). The combined organic layers were dried over MgSO$_4$ and concentrated to give the compound as a tan oil (13.7 g, 73.9% yield). LRMS (ESI) m/z 244 [(M+H)$^+$; calcd for C$_{12}$H$_{22}$NO$_4$ 244].

The following carbamate intermediates (B3-B31) can be prepared using the chemistry described for the preparation of (2S)-3,3-dimethyl-2-{[(pent-4-en-1-yloxy)carbonyl] amino}butanoic acid (B2), by utilizing the appropriate amino acid and alcohol or the preparation of N-[(Pent-4-en-1-yloxy) carbonyl]-L-norleucine (B1) by utilizing the appropriate alcohol and amino ester.

| Int. | Amino Acid | Alcohol | Structure | Name | LRMS (M + H)$^+$ |
|---|---|---|---|---|---|
| B3 | L-Valine | 4-Penten-1-ol | 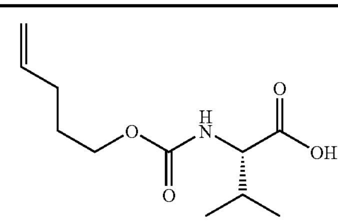 | N-[(Pent-4-en-1-yloxy)carbonyl]-L-valine | 230.3 |

-continued

| Int. | Amino Acid | Alcohol | Structure | Name | LRMS (M + H)+ |
|---|---|---|---|---|---|
| B4 | L-t-Butyl-glycine | 2,2-Dimethyl-4-penten-1-ol Ref: J. Org. Chem (1981) 46, 1177-1182. | 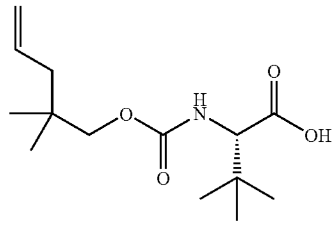 [SMILES: C=CCC(C)(C)COC(=O)N[C@H](C(=O)O)C(C)(C)C] | N-{[(2,2-Dimethylpent-4-en-1-yl)oxy]carbonyl}-3-methyl-L-valine | 272.3 |
| B5 | L-t-Butyl-glycine | 5-Hexen-1-ol | 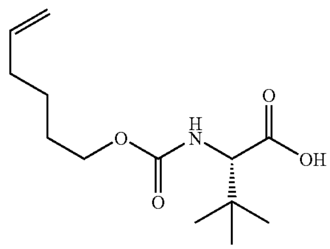 [SMILES: C=CCCCCOC(=O)N[C@H](C(=O)O)C(C)(C)C] | N-[(Hex-5-en-1-yloxy)carbonyl]-3-methyl-L-valine | 258.3 |
| B6 | L-t-Butyl-glycine | 4-Hepten-1-ol | 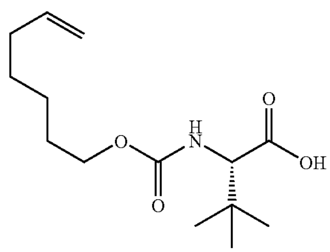 [SMILES: C=CCCCCCOC(=O)N[C@H](C(=O)O)C(C)(C)C] | N-[(Hept-6-en-1-yloxy)carbonyl]-3-methyl-L-valine | 272.3 |
| B7 | L-Cyclohexyl-glycine | 4-Penten-1-ol | 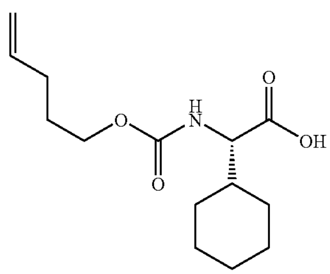 [SMILES: C=CCCCOC(=O)N[C@H](C(=O)O)C1CCCCC1] | (2S)-Cyclohexyl{[(pent-4-en-1-yloxy)carbonyl]amino}acetic acid | 270.3 |
| B8 | L-Cyclopentyl-glycine | 4-Penten-1-ol | 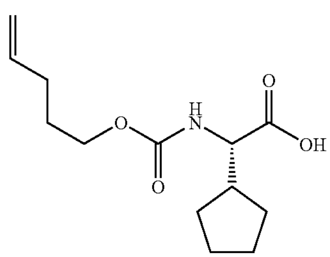 [SMILES: C=CCCCOC(=O)N[C@H](C(=O)O)C1CCCC1] | (2S)-Cyclopentyl{[(pent-4-en-1-yloxy)carbonyl]amino}acetic acid | 256.3 |
| B9 | L-Cyclohexyl-glycine | 2,2-Dimethyl-4-penten-1-ol Ref: J Org. Chem (1981), 46, 1177-1182. | 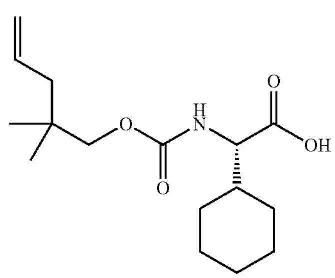 [SMILES: C=CCC(C)(C)COC(=O)N[C@H](C(=O)O)C1CCCCC1] | (2S)-Cyclohexyl({[(2,2-dimethylpent-4-en-1-yl)oxy]carbonyl}amino)acetic acid | 298.3 |

| Int. | Amino Acid | Alcohol | Structure | Name | LRMS (M + H)+ |
|---|---|---|---|---|---|
| B10 | L-Cyclopentyl-glycine | 2,2-Dimethyl-4-penten-1-ol Ref: J. Org. Chem (1981) 46, 1177-1182. | 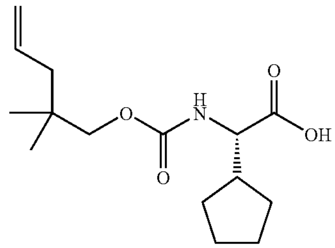 [SMILES: C=CCC(C)(C)COC(=O)N[C@H](C(=O)O)C1CCCC1] | (2S)-Cyclopentyl({[(2,2-dimethylpent-4-en-1-yl)oxy]carbonyl}amino)acetic acid | 284.3 |
| B11 | L-t-Butyl-glycine | 2,2-Dimethylhex-5-en-1-ol Ref: J. Org. Chem. (1991), 56, 1623. | 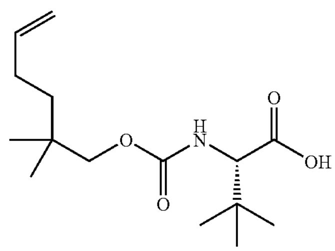 [SMILES: C=CCCC(C)(C)COC(=O)N[C@H](C(=O)O)C(C)(C)C] | N-{[(2,2-Dimethylhex-5-en-1-yl)oxy]carbonyl}-3-methyl-L-valine | 286.3 |
| B12 | L-Cyclohexyl-glycine | 6-Hepten-1-ol | 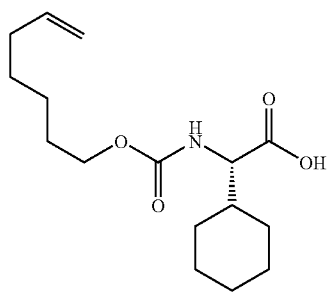 [SMILES: C=CCCCCCOC(=O)N[C@H](C(=O)O)C1CCCCC1] | (2S)-Cyclohexyl{[(hept-6-en-1-yloxy)carbonyl]amino}acetic acid | 298.3 |
| B13 | L-Cyclohexyl-glycine | 5-Hexen-1-ol | 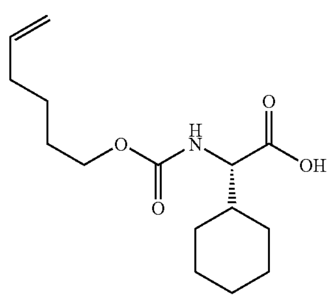 [SMILES: C=CCCCCOC(=O)N[C@H](C(=O)O)C1CCCCC1] | (2S)-Cyclohexyl{[(hex-5-en-1-yloxy)carbonyl]amino}acetic acid | 284.4 |
| B14 | L-Cyclopentyl-glycine | 5-Hexen-1-ol | 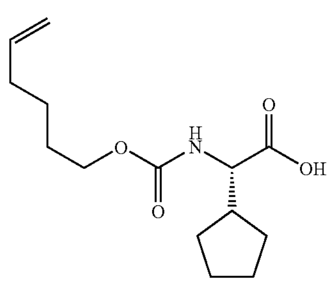 [SMILES: C=CCCCCOC(=O)N[C@H](C(=O)O)C1CCCC1] | (2S)-Cyclopentyl{[(hex-5-en-1-yloxy)carbonyl]amino}acetic acid | 270.3 |

-continued

| Int. | Amino Acid | Alcohol | Structure | Name | LRMS (M + H)+ |
|---|---|---|---|---|---|
| B15 | L-Cyclopentyl-glycine | 2,2-Dimethylhex-5-en-1-ol Ref: J. Org. Chem. (1991), 56, 1623. | 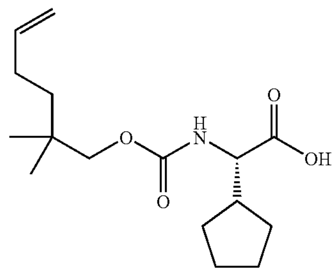 [SMILES: C=CCCC(C)(C)COC(=O)N[C@H](C(=O)O)C1CCCC1] | (2S)-Cyclopentyl({[(2,2-dimethylhex-5-en-1-yl)oxy]carbonyl}amino)acetic acid | 298.3 |
| B16 | L-Cyclohexyl-glycine | 2,2-Dimethylhex-5-en-1-ol Ref: J. Org. Chem. (1991), 56, 1623. | 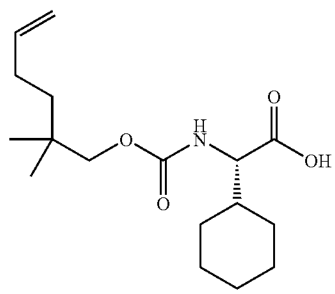 [SMILES: C=CCCC(C)(C)COC(=O)N[C@H](C(=O)O)C1CCCCC1] | (2S)-Cyclohexyl({[(2,2-dimethylhex-5-en-1-yl)oxy]carbonyl}amino)acetic acid | 312.3 |
| B17 | L-Cyclohexyl-glycine | 2-Methylpent-4-en-1-ol Ref: Tetrahedron (1993), 49, 947. | 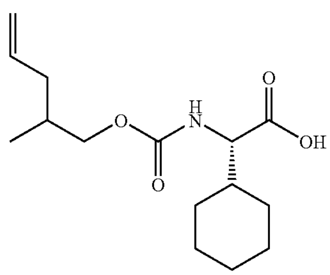 [SMILES: C=CCC(C)COC(=O)N[C@H](C(=O)O)C1CCCCC1] | (2S)-Cyclohexyl({[(2-methylpent-4-en-1-yl)oxy]carbonyl}amino)acetic acid | 284.4 |
| B18 | L-t-Butyl-glycine | 2-Methylpent-4-en-1-ol Ref: Tetrahedron (1993), 49, 947. | 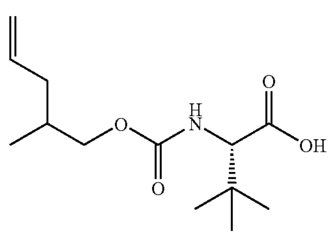 [SMILES: C=CCC(C)COC(=O)N[C@H](C(=O)O)C(C)(C)C] | 3-Methyl-N-{[(2-methylpent-4-en-1-yl)oxy]carbonyl}-L-valine | 258.3 |
| B19 | L-Cyclopentyl-glycine | 2-Methylpent-4-en-1-ol Ref: Tetrahedron (1993), 49, 947. | 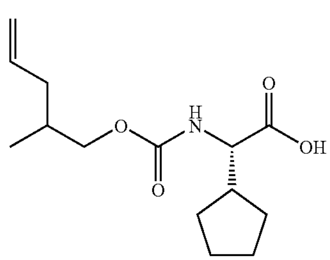 [SMILES: C=CCC(C)COC(=O)N[C@H](C(=O)O)C1CCCC1] | (2S)-Cyclopentyl({[(2-methylpent-4-en-1-yl)oxy]carbonyl}amino)acetic acid | 270.2 |
| B20 | L-Valine | 2-Methylpent-4-en-1-ol Ref: Tetrahedron (1993), 49, 947. | 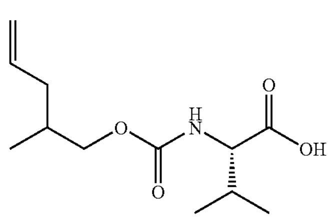 [SMILES: C=CCC(C)COC(=O)N[C@H](C(=O)O)C(C)C] | N-{[(2-methylpent-4-en-1-yl)oxy]carbonyl}-L-valine | |

-continued

| Int. | Amino Acid | Alcohol | Structure | Name | LRMS (M + H)+ |
|---|---|---|---|---|---|
| B21 | L-Valine | 2,2-Dimethyl-4-penten-1-ol Ref: J. Org. Chem (1981), 46, 1177-1182.. | 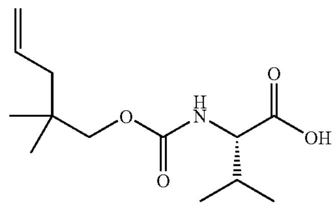 [SMILES: C=CCC(C)(C)COC(=O)N[C@H](C(=O)O)C(C)C] | N-{[(2,2-dimethylpent-4-en-1-yl)oxy]carbonyl}-L-valine | |
| B22 | L-Valine | 2,2-Dimethylhex-5-en-1-ol Ref: J. Org. Chem. (1991), 56, 1623. | 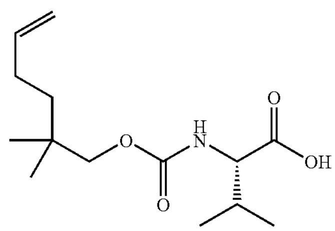 [SMILES: C=CCCC(C)(C)COC(=O)N[C@H](C(=O)O)C(C)C] | N-{[(2,2-dimethylhex-5-en-1-yl)oxy]carbonyl}-L-valine | |
| B23 | L-Valine | 5-Hexen-1-ol | 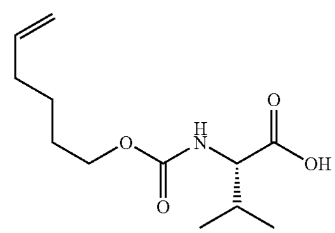 [SMILES: C=CCCCCOC(=O)N[C@H](C(=O)O)C(C)C] | N-[(hex-5-en-1-yloxy)carbonyl]-L-valine | |
| B24 | L-Valine | 2(S)-2-methyl-5-hexen-1-ol Ref: J. Org. Chem. (1992), 57, 2888. | | N-({[(2S)-2-methylhex-5-en-1-yl]oxy}carbonyl)-L-valine | |
| B24 | L-Valine | 2(R)-2-methyl-5-hexen-1-ol Ref: J. Am. Chem. Soc. (1991), 113, 5337. | | N-({[(2R)-2-methylhex-5-en-1-yl]oxy}carbonyl)-L-valine | |
| B25 | L-t-Butyl-glycine | 4-Penten-1-ol | 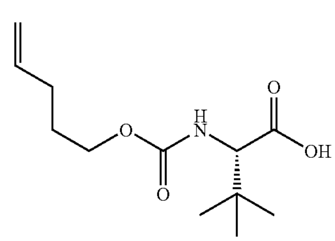 [SMILES: C=CCCCOC(=O)N[C@H](C(=O)O)C(C)(C)C] | N-[(Pent-4-en-1-yloxy)carbonyl]-3-methyl-L-valine | |

-continued

| Int. | Amino Acid | Alcohol | Structure | Name | LRMS (M + H)+ |
|---|---|---|---|---|---|
| B26 | L-Cyclopentyl-glycine | 2(S)-2-methyl-5-hexen-1-ol Ref: J. Org. Chem. (1992), 57, 2888. | 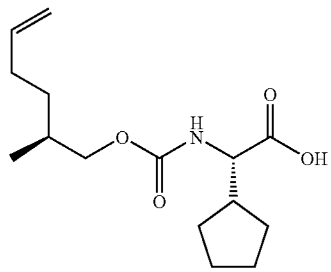 [SMILES: C=CCC[C@H](C)COC(=O)N[C@H](C(=O)O)C1CCCC1] | (2S)-cyclopentyl[({[(2S)-2-methylhex-5-en-1-yl]oxy}carbonyl)amino]acetic acid | |
| B27 | L-Cyclopentyl-glycine | 2(R)-2-methyl-5-hexen-1-ol Ref: J. Am. Chem. Soc. (1991), 113, 5337. | 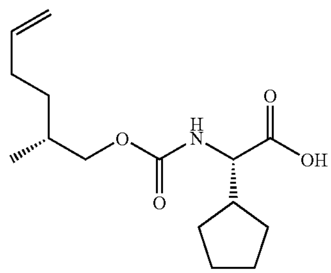 [SMILES: C=CCC[C@@H](C)COC(=O)N[C@H](C(=O)O)C1CCCC1] | (2R)-cyclopentyl[({[(2S)-2-methylhex-5-en-1-yl]oxy}carbonyl)amino]acetic acid | |
| B28 | L-Cyclohexyl-glycine | 2(S)-2-methyl-5-hexen-1-ol Ref: J. Org. Chem. (1992), 57, 2888. | 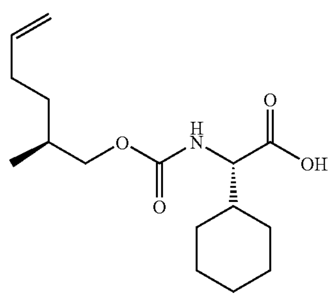 [SMILES: C=CCC[C@H](C)COC(=O)N[C@H](C(=O)O)C1CCCCC1] | (2S)-cyclohexyl[({[(2S)-2-methylhex-5-en-1-yl]oxy}carbonyl)amino]acetic acid | |
| B29 | L-Cyclohexyl-glycine | 2(R)-2-methyl-5-hexen-1-ol Ref: J. Am. Chem. Soc. (1991), 113, 5337. | 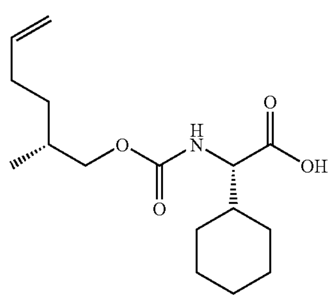 [SMILES: C=CCC[C@@H](C)COC(=O)N[C@H](C(=O)O)C1CCCCC1] | (2R)-cyclohexyl[({[(2S)-2-methylhex-5-en-1-yl]oxy}carbonyl)amino]acetic acid | |
| B30 | L-t-Butylglycine | 2(S)-2-methyl-5-hexen-1-ol Ref: J. Org. Chem. (1992), 57, 2888. | 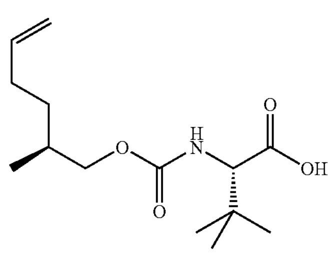 [SMILES: C=CCC[C@H](C)COC(=O)N[C@H](C(=O)O)C(C)(C)C] | 3-methyl-N-({[(2S)-2-methylhex-5-en-1-yl]oxy}carbonyl)-L-valine | |

| Int. | Amino Acid | Alcohol | Structure | Name | LRMS (M + H)+ |
|---|---|---|---|---|---|
| B31 | L-t-Butylglycine | 2(R)-2-methyl-5-hexen-1-ol Ref: J. Am. Chem. Soc. (1991), 113, 5337. | 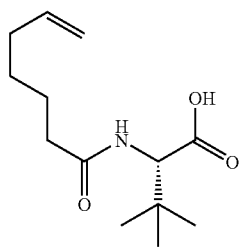 [SMILES: C=CCCCCC(=O)N[C@H](C(=O)O)C(C)(C)C] | 3-methyl-N-({[(2R)-2-methylhex-5-en-1-yl]oxy}carbonyl)-L-valine | |

Intermediate B32:
N-Hept-6-enoyl-3-methyl-L-valine

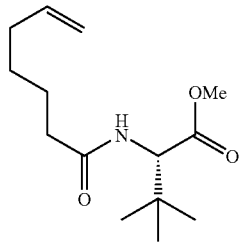 [SMILES: C=CCCCCC(=O)N[C@H](C(=O)OC)C(C)(C)C]

Step 1: Methyl N-Hept-6-enoyl-3-methyl-L-valinate

A solution of L-t-leucine methyl ester (1.00 g, 6.89 mmol), 6-heptenoic acid (1.06 g, 8.26 mmol), EDC (1.58 g, 8.26 mmol) and HOAt (1.23 g, 8.26 mmol) in DMF (10 mL) was stirred at 22° C. for 2 hours. The reaction mixture was diluted with aqueous saturated NaHCO$_3$ (30 mL), and extracted with EtOAc (3×50 mL). The combined organic layers were washed with water (3×30 mL), brine (20 mL), dried over Na$_2$SO$_4$, filtered and concentrated. The residue was chromatographed on silica gel, eluting with 5-50% EtOAc/hexane, to give the title product (1.42 g, 81%). LRMS (ESI) m/z 256.3 [(M+H)$^+$; calcd for C$_{14}$H$_{26}$NO$_3$: 256.2].

Step 2: N-Hept-6-enoyl-3-methyl-L-valine (Intermediate B32)

A solution of methyl N-hept-6-enoyl-3-methyl-L-valinate (1.40 g, 5.48 mmol) in THF (10 mL) and 1 N NaOH (10 mL) was stirred at 22° C. for 2 hours. The reaction mixture was acidified to pH 3 with 1 N HCl and extracted with EtOAc (3×150 mL). The combined EtOAc layers were washed with water (50 mL), brine (50 mL), dried over Na$_2$SO$_4$, filtered and concentrated to give the title product (1.12 g, 84%). LRMS (ESI) m/z 242.3 [(M+H)$^+$; calcd for C$_{13}$H$_{24}$NO$_3$: 242.2].

EXAMPLES

Example 1

[(1S,2R)-1-({[(5R,7S,10S)-10-tert-butyl-15,15-dimethyl-3,9,12-trioxo-6,7,9,10,11,12,14,15,16,17,18,19-dodecahydro-1H,5H-2, 23:5,8-dimethano-4,13,2,8,11-benzodioxatriazacyclohenicosin-7-yl]carbonyl}amino)-2-vinylcyclopropyl]phosphonic acid

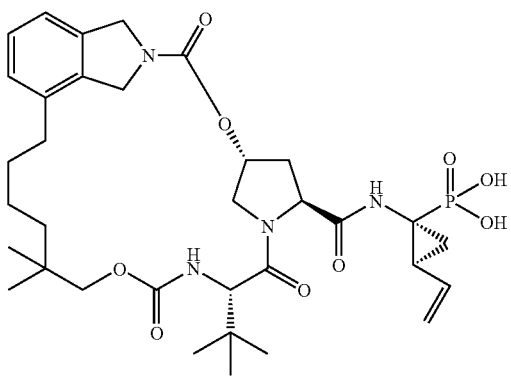 [SMILES: C=C[C@@H]1C[C@]1(NC(=O)[C@@H]1C[C@@H]2CN1C(=O)[C@H](C(C)(C)C)NC(=O)OCC(C)(C)CCCCc1cccc3c1CN(C3)C(=O)O2)P(=O)(O)O]

Step 1: 1-Bromo-2,3-bis(bromomethyl)benzene

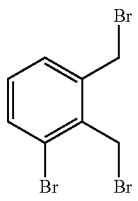 [SMILES: BrCc1cccc(Br)c1CBr]

To a suspension of 3-bromo-o-xylene (999 g, 5.40 mol) in chlorobenzene (9 L) at RT was added N-bromosuccinimide (1620 g, 9.1 mol) and benzoyl peroxide (2.6 g, 10.8 mmol).

The reaction mixture was heated to 80° C. and stirred under nitrogen for 18 hours. The reaction mixture was cooled to 70° C., and an additional portion of NBS (302 g, 1.7 mol) was added. The reaction mixture was heated to 80° C. and stirred under nitrogen for 22 hours. The reaction mixture was cooled to RT, diluted with heptane (6 L) and filtered. The filter cake was washed with heptane (4 L), and the combined filtrates were evaporated. The crude product was dissolved in heptane (2 L) and chloroform (200 mL) and filtered through basic alumina (500 g). The alumina pad was washed with heptane (4 L), and the combined filtrates were evaporated to give 1-bromo-2,3-bis(bromomethyl)benzene (1760 g, crude weight), which was used without further purification. $^1$H NMR (CDCl$_3$) δ (ppm) 7.56 (d, J=8.0 Hz, 1 H), 7.31 (d, J=8.0 Hz, 1 H), 7.26 (s, 1 H), 7.16 (t, J=8.0 Hz, 1 H), 4.84 (s, 2 H), 4.64 (s, 2 H).

Step 2: 2-Benzyl-4-bromoisoindoline hydrochloride

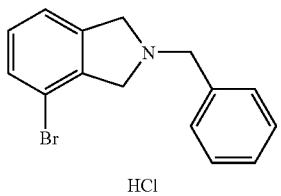 [SMILES: Brc1cccc2c1CN(Cc1ccccc1)C2 ; Cl]

HCl

Potassium bicarbonate (657 g, 6.56 mol) was suspended in MeCN (17 L), and the mixture was heated to 80° C. Solutions of crude 1-bromo-2,3-bis(bromomethyl)benzene (900 g, 2.63 mol in 1 L MeCN) and benzylamine (281 g, 2.63 mol in 1 L MeCN) were added concurrently via addition funnels over 2 hours. The reaction mixture was stirred at 77° C. for 2 hours, then cooled to RT and stirred for 16 hours. The contents of the reaction flask were cooled and filtered, and the solvent removed by evaporation. The reaction was partitioned between water (6 L) and EtOAc (2 L). The pH was adjusted to >9 by the addition of 1M K$_2$CO$_3$; the layers were separated; and the aqueous phase extracted with an additional portion of EtOAc (2 L). The combined organics were washed with brine, dried with anhydrous Na$_2$SO$_4$, filtered, and evaporated. The crude oil was diluted with EtOH (300 mL) and cooled to 0° C. Methanolic HCl was added until the mixture was acidic, and then MTBE (700 mL) was added. Then, the mixture was sonicated, then stirred for 15 hours. MTBE (1 L) was added, and the mixture was filtered and washed with 20% EtOH in MTBE followed by MTBE. The solid was air dried to give 2-benzyl-4-bromoisoindoline hydrochloride (211 g). An additional portion of product (86 g) was isolated by concentration of the mother liquors. LRMS (ESI) m/z 289 [(M+H)$^+$; calcd for C$_{15}$H$_{15}$BrN: 289].

Step 3: 4-Bromoisoindoline

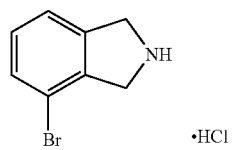

·HCl

To a solution of 2-benzyl-4-bromoisoindoline hydrochloride (11 g, 30.96 mmol) in 200 mL EtOAc was added 1M NaOH (100 mL) and the mixture stirred for 30 minutes. The organic layer was separated, washed with brine, dried over anhydrous Na$_2$SO$_4$ and solvent evaporated to an oil which was azeotroped once with PhMe (50 mL). The oil was dissolved in chlorobenzene (50 mL) and 4A molecular sieves (5 g) added to the stirred solution. After 10 minutes, 1-chloroethylchloroformate (5.6 mL, 51 mmol) was added dropwise over 5 minutes. The reaction mixture was then heated to 90° C. for 2 hours, cooled to RT and filtered. The solids were washed with chlorobenzene (5 mL) and MeOH (40 mL). The filtrate was heated to 70° C. for 1 hour, allowed to cool and stirred at RT overnight. The solids were filtered, washed with chlorobenzene (2 mL) and hexane and dried to give 6.84 g of title compound. LRMS (ESI) m/z 198.1 [(M+H)$^+$; calcd for C$_8$H$_9$BrN: 198.0].

Step 4: 1-t-Butyl 2-methyl (2S,4R)-4-{[(4-bromo-1,3-dihydro-2H-isoindol-2-yl)carbonyl]oxy}pyrrolidine-1,2-dicarboxylate

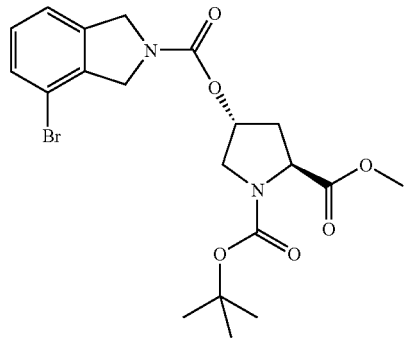 [SMILES: COC(=O)[C@@H]1C[C@@H](OC(=O)N2Cc3cccc(Br)c3C2)CN1C(=O)OC(C)(C)C]

To a solution of (2S,4R)-BOC-4-hydroxyproline methyl ester (126.3 g, 515 mmol) in DMF (960 mL) at 0° C. was added N,N'-carbonyldiimidazole (83.51 g, 515 mmol). The reaction mixture was stirred at RT for 3 hours. 4-Bromoisoindoline hydrochloride (120 g, 515 mmol) and DIPEA (96.3 mL, 540 mmol) were added, and the reaction mixture heated to 50° C. for 6 hours. The reaction mixture was then allowed to cool to RT and stirred overnight. The reaction mixture was partitioned between EtOAc (3 L) and 10% aqueous KHSO$_4$ (6 L), the aqueous re-extracted with EtOAc (2 L) and the combined organic phases washed with 10% aqueous NaHCO$_3$, brine, dried over Na$_2$SO$_4$ and solvent evaporated to a foam (239 g). LRMS (ESI) m/z 471.0 [(M+H)$^+$; calcd for C$_{20}$H$_{26}$BrN$_2$O$_6$: 471.1].

Step 5: 1-t-Butyl 2-methyl (2S,4R)-4-{[(4-vinyl-1,3-dihydro-2H-isoindol-2-yl)carbonyl]oxy}pyrrolidine-1,2-dicarboxylate

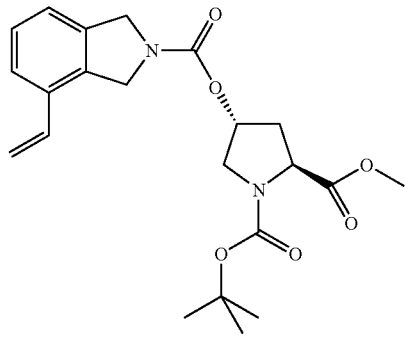 [SMILES: C=Cc1cccc2c1CN(C(=O)O[C@@H]1C[C@@H](C(=O)OC)N(C(=O)OC(C)(C)C)C1)C2]

To a solution of 1-t-butyl 2-methyl (2S,4R)-4-{[(4-bromo-1,3-dihydro-2H-isoindol-2-yl)carbonyl]oxy}pyrrolidine-1,2-dicarboxylate (10.0 g, 21.3 mmol) in EtOH (200 mL) was added potassium vinyltrifluoroborate (4.28 g, 32 mmol) and Et₃OH (4.5 mL, 32 mmol) followed by dichloro[1,1-bis(diphenylphosphino)ferrocene]palladium (II) chloride dichloromethane adduct (175 mg, 0.21 mmol). The reaction mixture was heated to reflux for 6 hours, cooled to RT, diluted with 10% aqueous KHSO₄. The EtOH was removed by evaporation in vacuo. The aqueous residue was extracted with EtOAc, and the organic phase washed with brine, dried over Na₂SO₄. The solvent was evaporated, and the crude product was purified by chromatography on silica eluting with 40-60% EtOAc/hexane to give, after evaporation, the title compound (8.18 g). LRMS (ESI) m/z 417.2 [(M+H)$^+$; calcd for $C_{22}H_{29}N_2O_6$: 417.2].

Step 6: (3R,5S)-5-(Methoxycarbonyl)pyrrolidin-3-yl-4-vinyl-1,3-dihydro-2H-isoindole-2-carboxylate hydrochloride

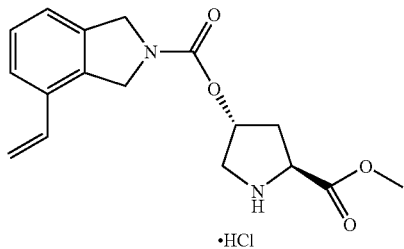 [SMILES: C=Cc1cccc2c1CN(C(=O)O[C@H]1CN[C@H](C(=O)OC)C1)C2 ; Cl]

A mixture of 1-t-butyl 2-methyl (2S,4R)-4-{[(4-vinyl-1,3-dihydro-2H-isoindol-2-yl)carbonyl]oxy}pyrrolidine-1,2-dicarboxylate (18.0 g, 43.2 mmol) and HCl/dioxane (4 M) (43.2 mL, 173 mmol) was stirred at RT for 2 hours. The reaction mixture was concentrated to remove the dioxane, followed by concentration from Et₂O to give (3R,5S)-5-(methoxycarbonyl)pyrrolidin-3-yl-4-vinyl-1,3-dihydro-2H-isoindole-2-carboxylate hydrochloride as an off-white solid (15 g), which was used without further purification. LRMS (ESI) m/z 317 [(M+H)$^+$; calcd for $C_{17}H_{21}N_2O_4$: 317].

Step 7: Methyl N-{[(2,2-dimethylhex-5-en-1-yl)oxy]carbonyl}-3-methyl-L-valyl-(4R)-4-{[(4-vinyl-1,3-dihydro-2H-isoindol-2-yl)carbonyl]oxy}-L-prolinate

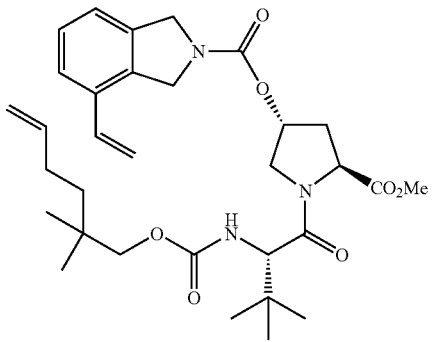 [SMILES: C=CCCC(C)(C)COC(=O)N[C@H](C(=O)N1C[C@H](OC(=O)N2Cc3cccc(C=C)c3C2)C[C@H]1C(=O)OC)C(C)(C)C]

To a solution of (3R,5S)-5-(methoxycarbonyl)pyrrolidin-3-yl 4-vinyl-1,3-dihydro-2H-isoindole-2-carboxylate hydrochloride (5.0 g, 14.2 mmol) and Intermediate B11 (4.0 g, 14.2 mmol) in DMF (20 ml) at RT was added DIPEA (2.5 mL, 14.2 mmol), EDC (5.5 g, 28.4 mmol), and HOAt (1.9 g, 14.2 mmol). After 18 hours, the reaction mixture was poured into Et₂O and extracted with 1 N HCl. The aqueous layer was extracted with EtOAc, and the combined organic layers were washed with 1 N HCl, water, NaHCO₃, and brine. The organic layer was dried over MgSO₄, and the solvent was removed in vacuo. The crude product was purified on silica (30% EtOAc in hexanes) to yield 4.2 g of the title compound as a thick oil. LRMS (ESI) m/z 584.4 [(M+H)$^+$; calcd for $C_{32}H_{46}N_3O_7$: 584.3].

Step 8: Methyl (5R,7S,10S,18E)-10-t-butyl-15,15-dimethyl-3,9,12-trioxo-6,7,9,10,11,12,14,15,16,17-decahydro-1H,5H-2, 23:5,8-dimethano-4,13,2,8,11-benzodioxatriazacyclohenicosine-7-carboxylate

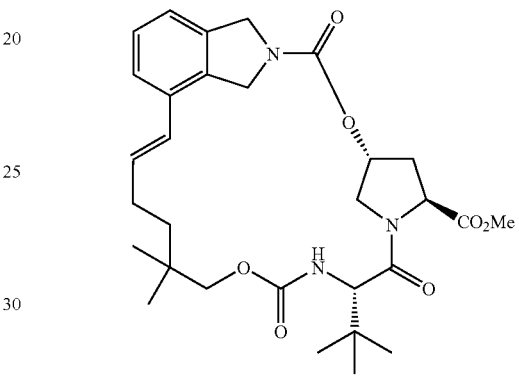

To a solution of methyl N-{[(2,2-dimethylhex-5-en-1-yl)oxy]carbonyl}-3-methyl-L-valyl-(4R)-4-{[(4-vinyl-1,3-dihydro-2H-isoindol-2-yl)carbonyl]oxy}-L-prolinate (4.7 g, 8.05 mmol) in degassed (nitrogen bubbling for 30 min) DCM (1410 mL) was added Zhan 1B catalyst (Zhan catalyst 1B, RC-303, Zannan Pharma Ltd.) (0.591 g, 0.805 mmol). The mixture was then stirred at RT under an N₂ atmosphere. After 19 hours, the reaction was complete, and DMSO (57 μL, 0.805 mmol) was added. The mixture was stirred for 2 hours, and the mixture was concentrated in vacuo to ~70 mL. The crude product was then directly purified on silica (gradient elution, 0-50% EtOAc in hexanes) to yield 4.4 g of the title compound as an oil. LRMS (ESI) m/z 556.3 [(M+H)$^+$; calcd for $C_{30}H_{42}N_3O_7$: 556.3].

Step 9: Methyl (5R,7S,10S)-10-t-butyl-15,15-dimethyl-3,9,12-trioxo-6,7,9,10,11,12,14,15,16,17,18,19-dodecahydro-1H,5H-2,23:5,8-dimethano-4,13,2,8,11-benzodioxatriazacyclohenicosine-7-carboxylate

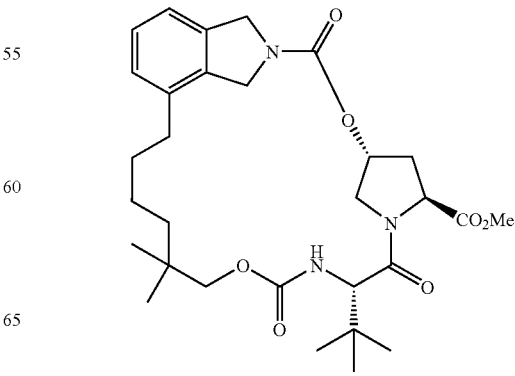

To a solution of methyl (5R,7S,10S,18E)-10-t-butyl-15, 15-dimethyl-3,9,12-trioxo-6,7,9,10,11,12,14,15,16,17-decahydro-1H,5H-2, 23:5,8-dimethano-4,13,2,8,11-benzodioxatriaza-cyclohenicosine-7-carboxylate (4.4 g, 7.92 mmol) in EtOAc (79 mL) was added Pd/C (0.421 g, 0.396 mmol). A H$_2$ balloon was then placed on the reaction flask. The flask was evacuated quickly and filled with H$_2$. After 17 hours, the reaction was complete as determined by LC-MS. The Pd/C was filtered through glass wool, and the crude product was purified on silica (gradient elution, 0-60% EtOAc in hexanes) to yield 4.01 g of the title compound as a white powder. LRMS (ESI) m/z 558.4 [(M+H)$^+$; calcd for C$_{30}$H$_{44}$N$_3$O$_7$: 558.3].

Step 10: (5R,7S,10S)-10-t-Butyl-15,15-dimethyl-3,9, 12-trioxo-6,7,9,10,11,12,14,15,16,17,18,19-dodecahydro-1H,5H-2, 23:5,8-dimethano-4,13,2,8, 11-benzodioxatriazacyclohenicosine-7-carboxylic acid

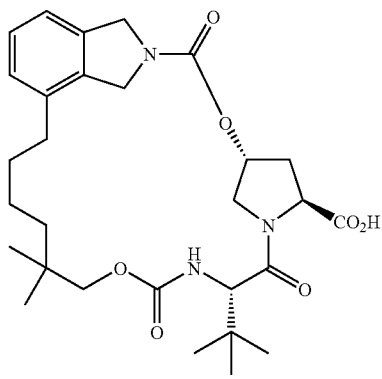 [SMILES: CC1(C)CCCCc2cccc3c2CN(C3)C(=O)O[C@@H]2C[C@@H](C(=O)O)N(C2)C(=O)[C@H](C(C)(C)C)NC(=O)OC1]

To a solution of methyl (5R,7S,10S)-10-t-butyl-15,15-dimethyl-3,9,12-trioxo-6,7,9,10,11,12,14,15,16,17,18,19-dodecahydro-1H,5H-2, 23:5,8-dimethano-4,13,2,8,11-benzodioxatriazacyclohenicosine-7-carboxylate (5.76 g, 10.33 mmol) in THF (41.3 mL), MeOH (41.3 mL), and water (20.7 mL) at RT was added LiOH (4.33 g, 103 mmol). After full conversion (45 minutes), as judged by LC-MS, the reaction was worked up by partitioning between Et$_2$O and 1 N HCl. The aqueous layer was then extracted with EtOAc. The combined organic layers were dried over MgSO$_4$, and the solvent was removed in vacuo to yield 5.53 g of the title compound, which was used without further purification. LRMS (ESI) m/z 544.4 [(M+H)$^+$; calcd for C$_{29}$H$_{42}$N$_3$O$_7$: 544.3].

Step 11: Diethyl[(1S,2R)-1-({[(5R,7S,10S)-10-t-butyl-15,15-dimethyl-3,9,12-trioxo-6,7,9,10,11,12, 14,15,16,17,18,19-dodecahydro-1H,5H-2, 23:5,8-dimethano-4,13,2,8,11-benzodioxatriazacyclohenicosin-7-yl] carbonyl}amino)-2-vinylcyclopropyl]phosphonic acid

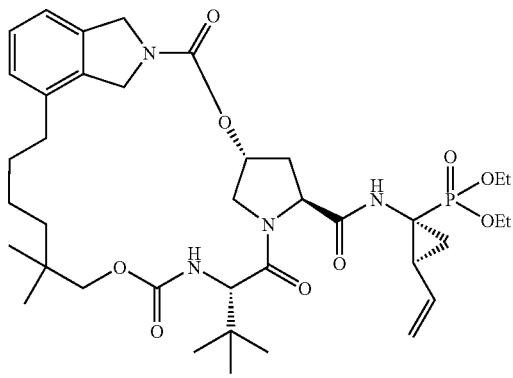 [SMILES: C=C[C@@H]1C[C@]1(NC(=O)[C@@H]1C[C@@H]2CN1C(=O)[C@H](C(C)(C)C)NC(=O)OCC(C)(C)CCCCc1cccc3c1CN(C3)C(=O)O2)P(=O)(OCC)OCC]

To a stirred solution of the product from Step 10 (160 mg, 0.294 mmol) in DCM 95 mL) was added N-methylmorpholine (0.081 mL, 0.74 mmol), Intermediate A1 (71 mg, 0.32 mmol) and HATU (123 mg, 0.32 mmol). The reaction mixture was stirred at RT for 18 hours, and directly purified by reverse-phase chromatography to give the title compound. LRMS (ESI) m/z 745.2 [(M+H)$^+$; [(M+H)$^+$; calcd for C$_{38}$H$_{58}$N$_4$O$_9$P: 745.4]

Step 12: [(1S,2R)-1-({[(5R,7S,10S)-10-t-butyl-15, 15-dimethyl-3,9,12-trioxo-6,7,9,10,11,12,14,15,16, 17,18,19-dodecahydro-1H,5H-2, 23:5,8-dimethano-4,13,2,8,11-benzodioxatriazacyclohenicosin-7-yl] carbonyl}amino)-2-vinylcyclopropyl]phosphonic acid

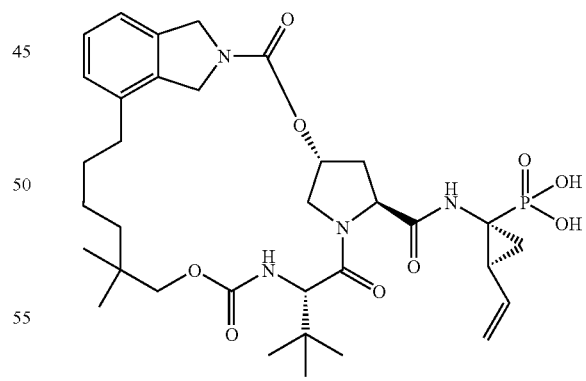

To a cooled (0° C.) solution of the product from Step 11 (1147 mg, 0.197 mmol.) and 2,6-lutidine (0.062 mL, 0.53 mmol) in CH$_3$CN (5 mL) was added trimethylsilyl iodide (0.073 mL, 0.54 mmol). The reaction mixture was stirred at 0° C. for 1 hour; MeOH and Et$_3$N were added; the volatiles evaporated; and the residue purified by chromatography to afford the title compound. LRMS (ESI) m/z 689.2 [(M+H)$^+$; [(M+H)$^+$; calcd for C$_{34}$H$_{50}$N4O$_9$P: 689.3]

By utilizing chemistry analogous to that described for Example 1, with the appropriate intermediates A and B, the following compounds can be prepared. Where appropriate the hydrogenation Step 9 is omitted.
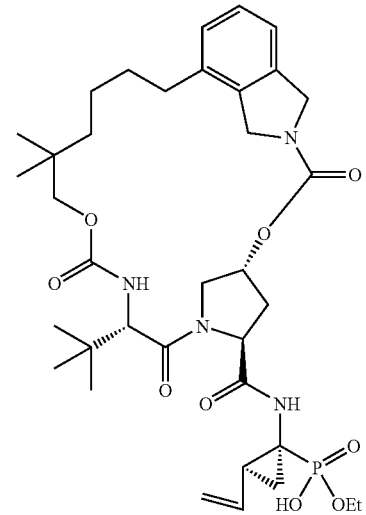
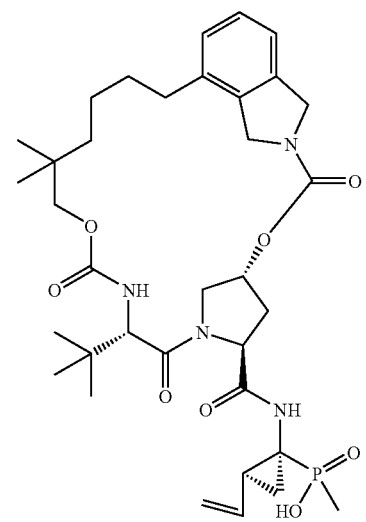
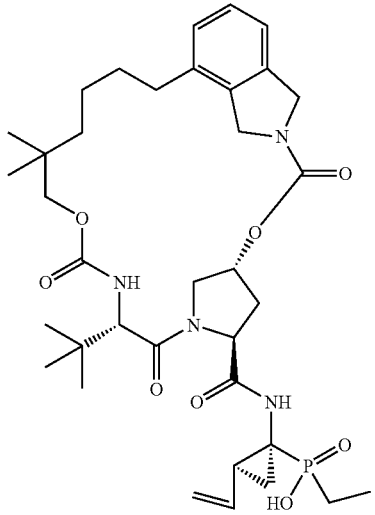
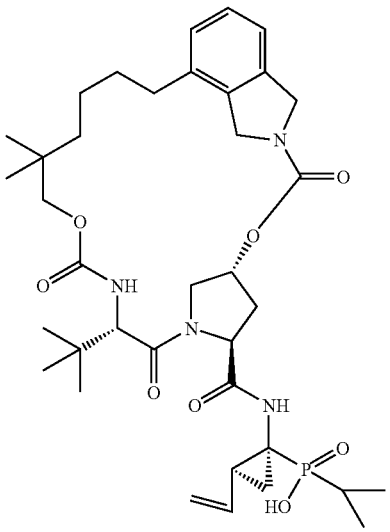
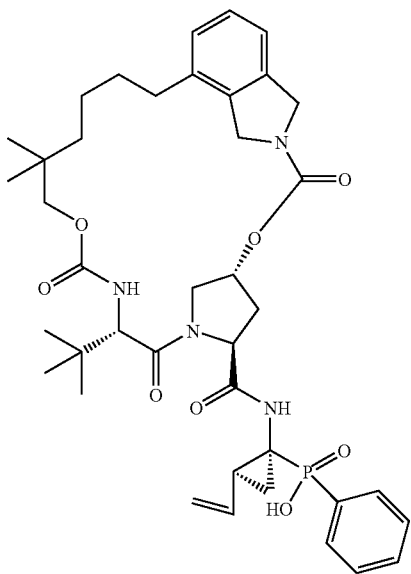
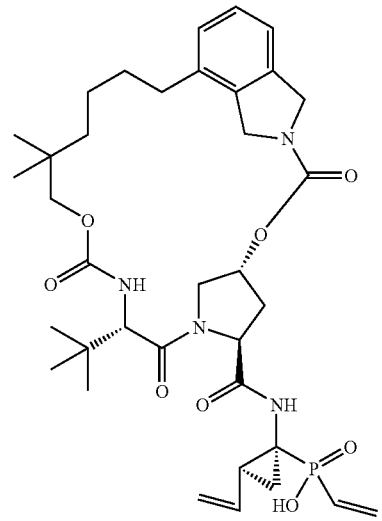

49
-continued
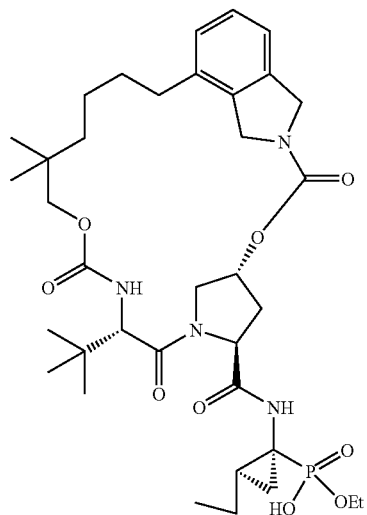
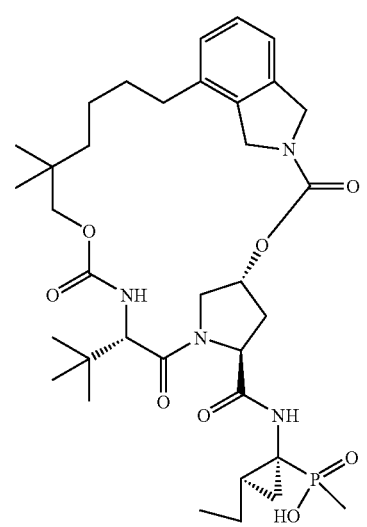
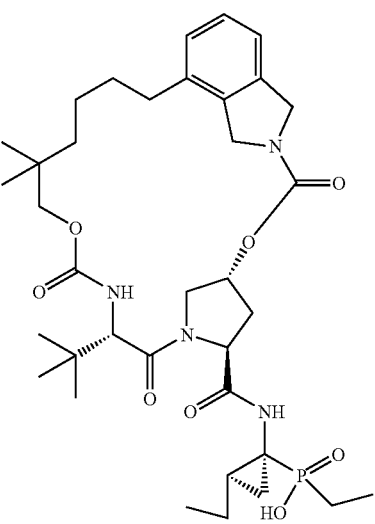
50
-continued
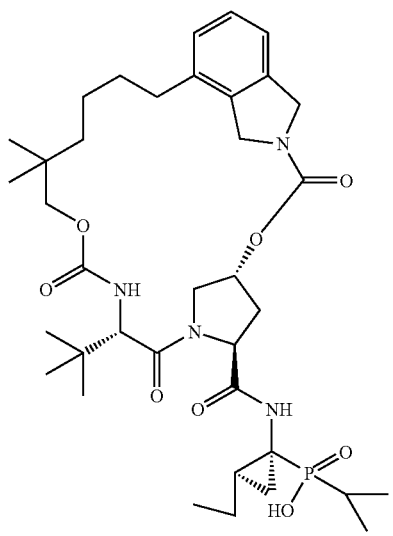
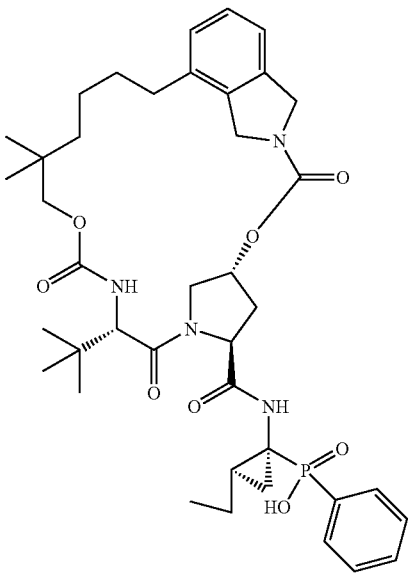
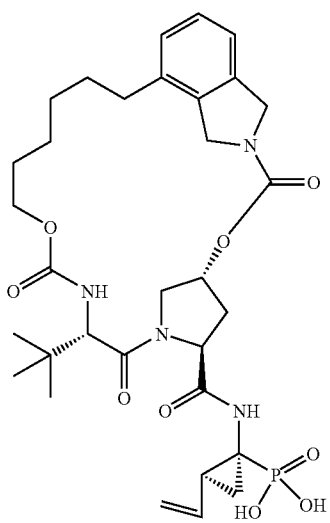

| 51 | 52 |
|---|---|
| -continued | -continued |
| 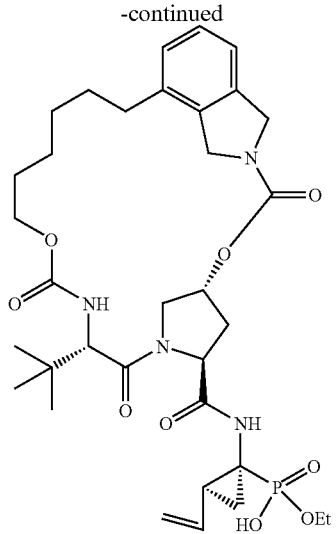 | 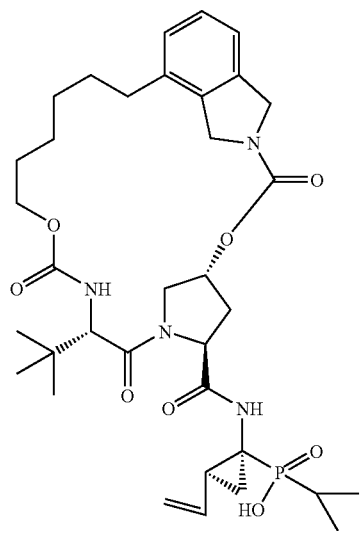 |
| 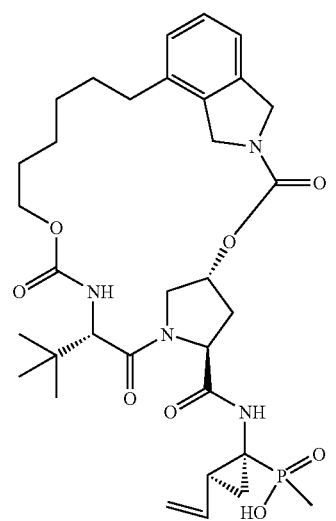 | 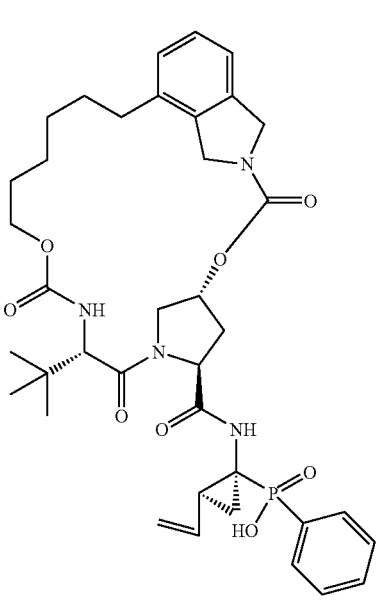 |
| 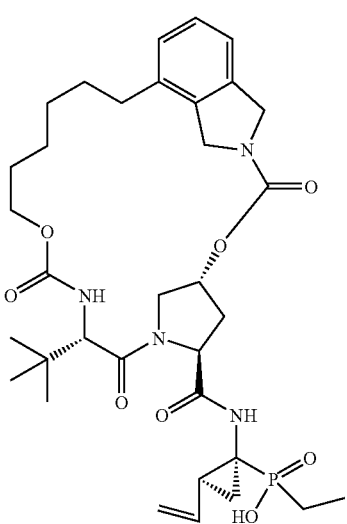 | 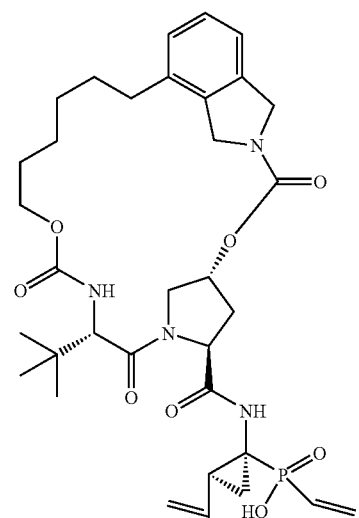 |

-continued
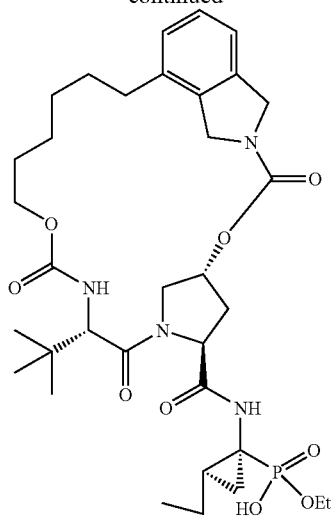
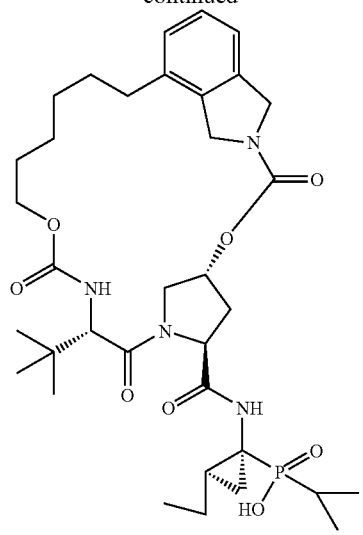
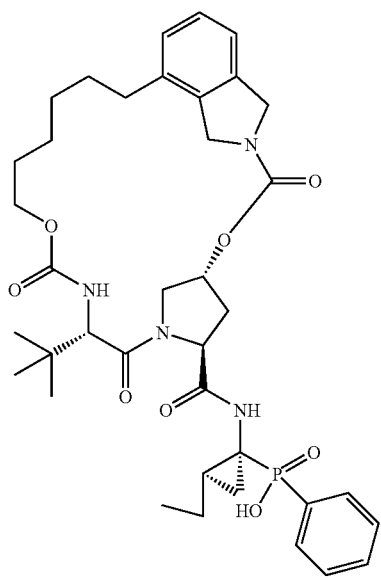
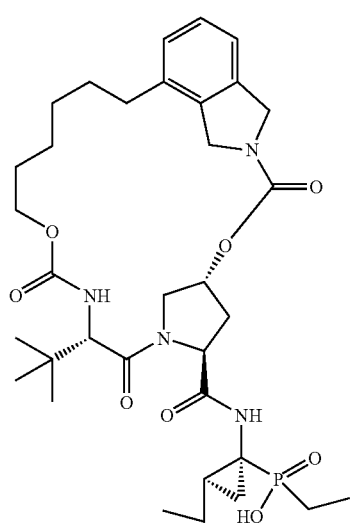
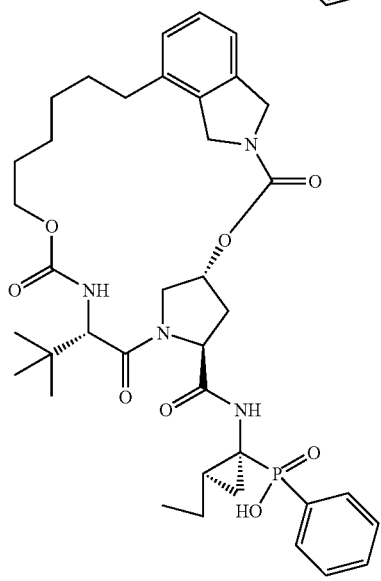

55
-continued
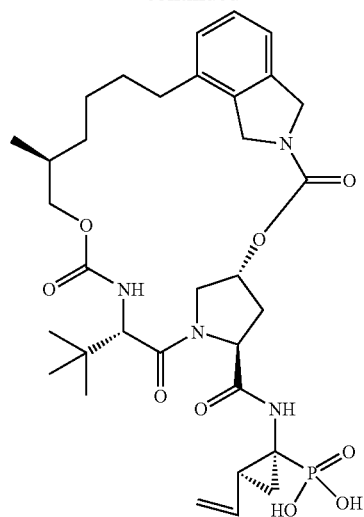
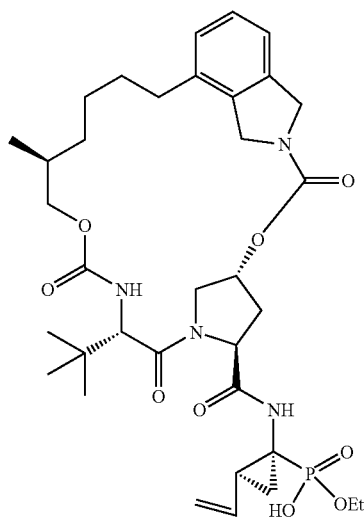
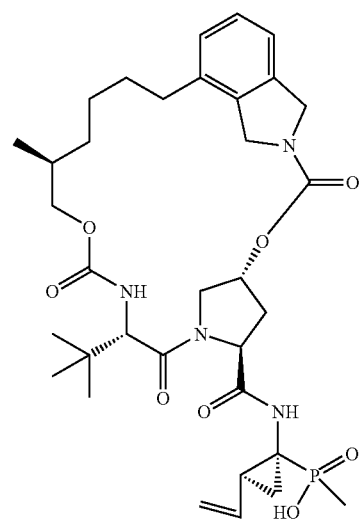
56
-continued
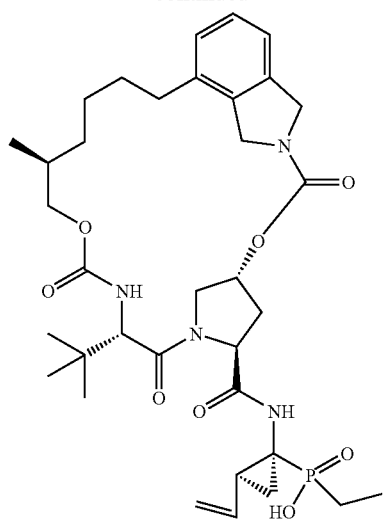
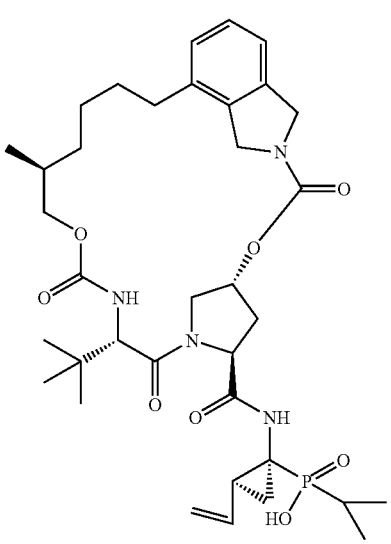
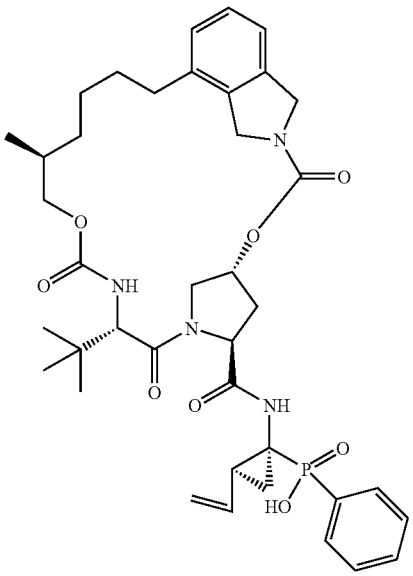

57
-continued
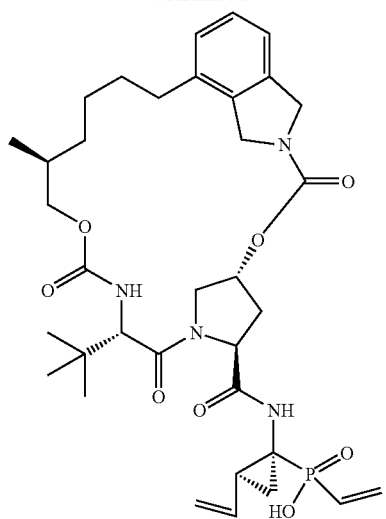
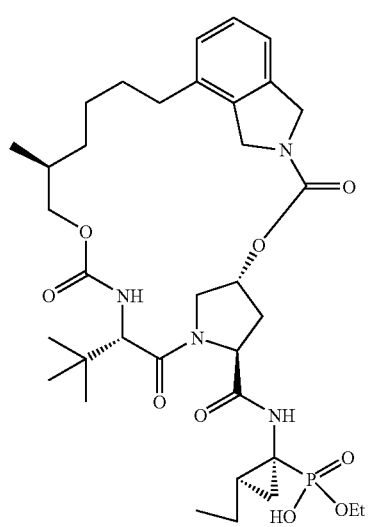
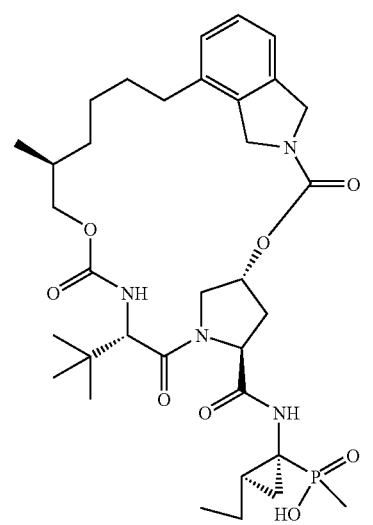
58
-continued
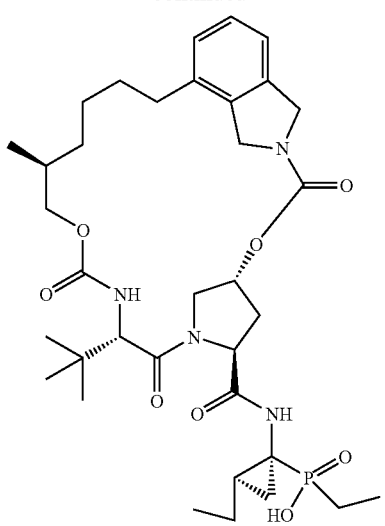
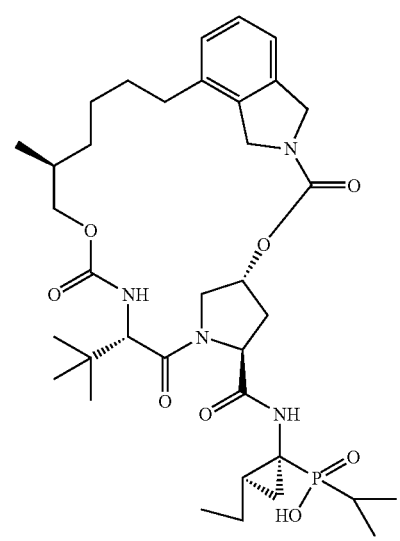

-continued
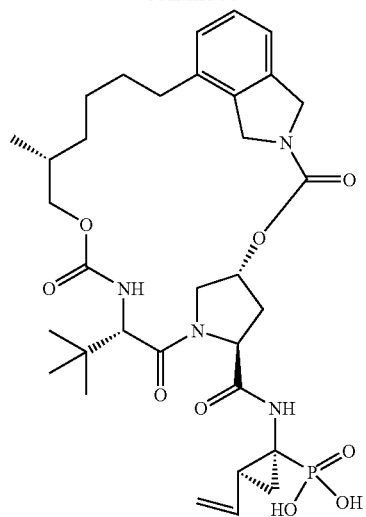
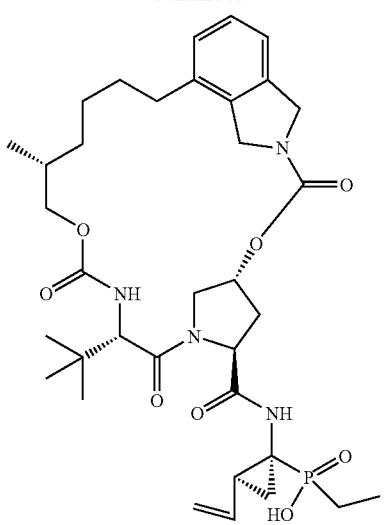
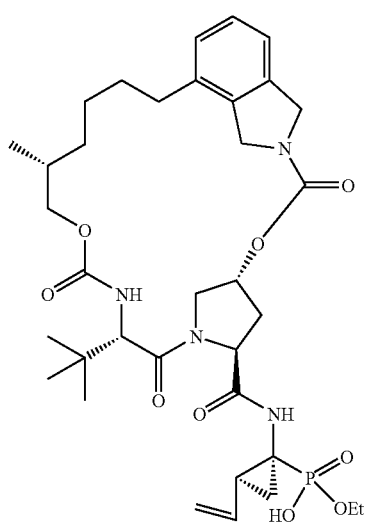
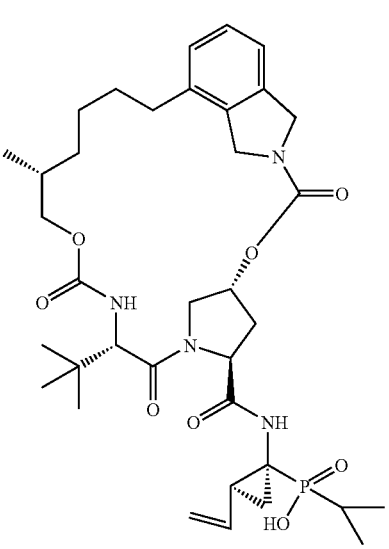
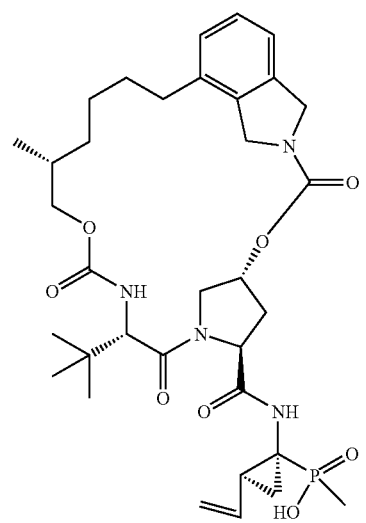
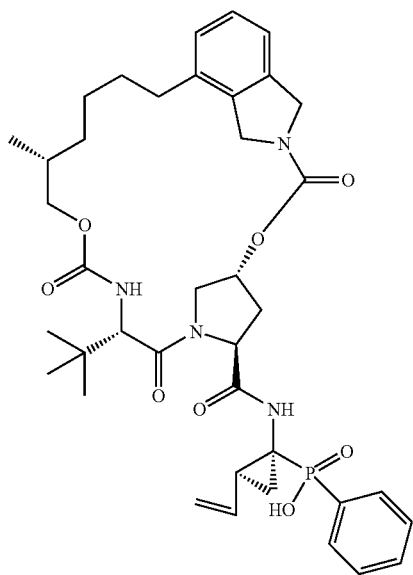

61
-continued
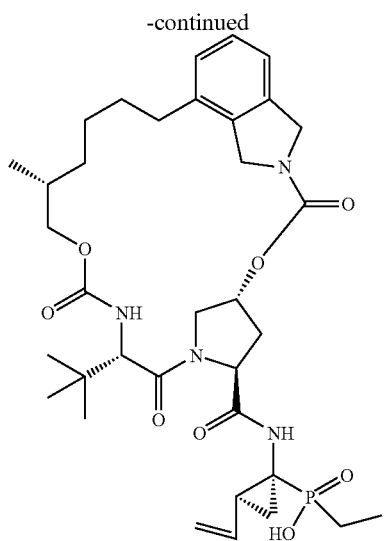
62
-continued
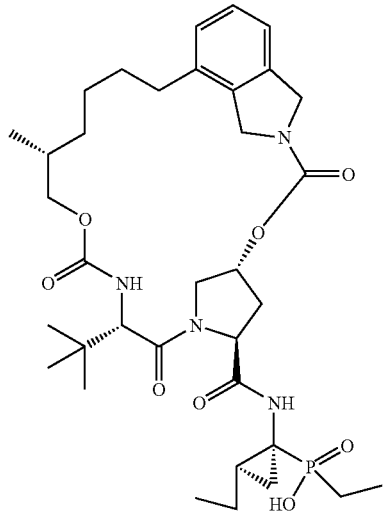
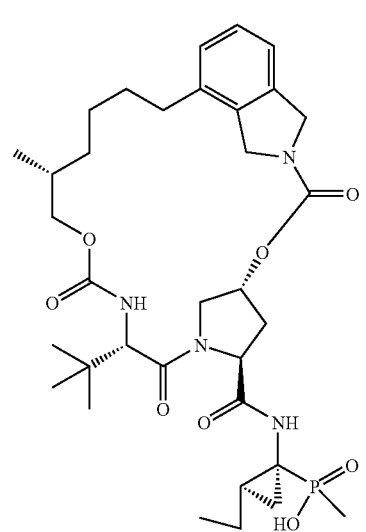
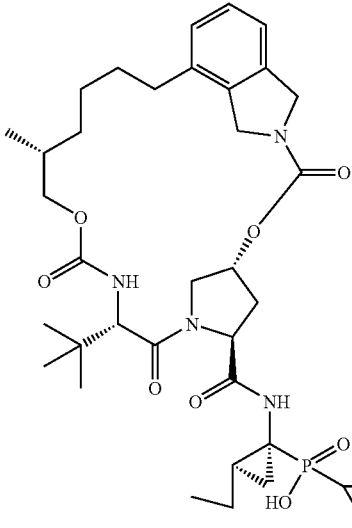
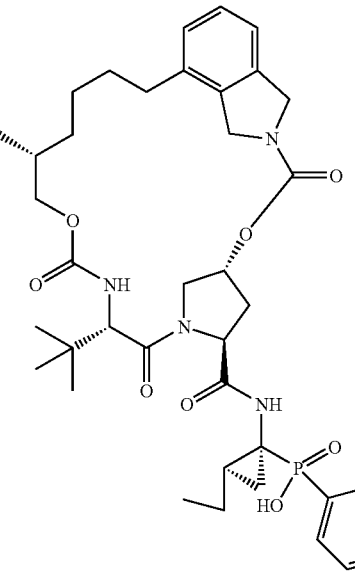
Other examples of the present invention are represented in the Table below in which $R^1$=vinyl or ethyl, $R^2$=OH, OEt, Me, Et, n-Pr, n-Bu, iPr, Ph or vinyl.

63
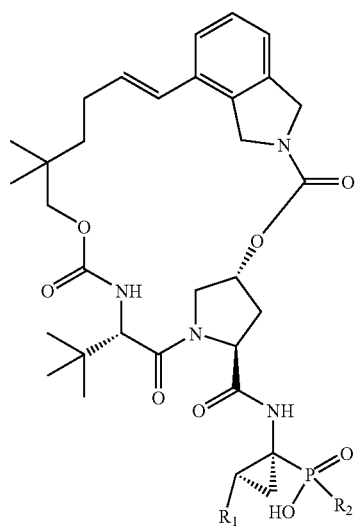
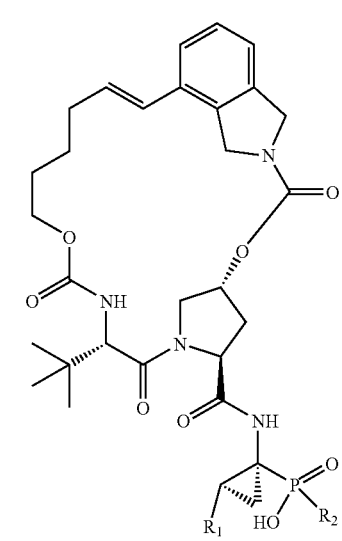
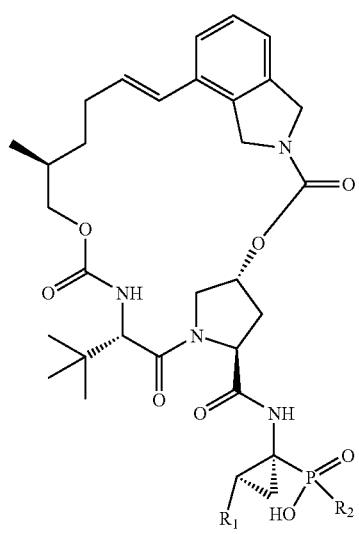
64
-continued
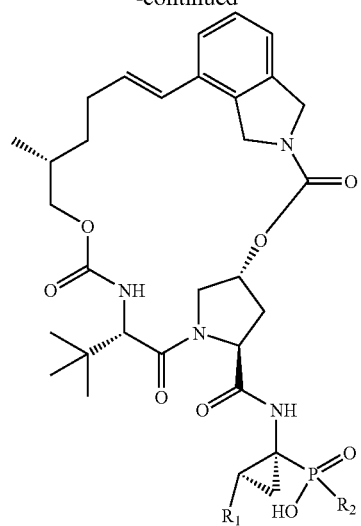
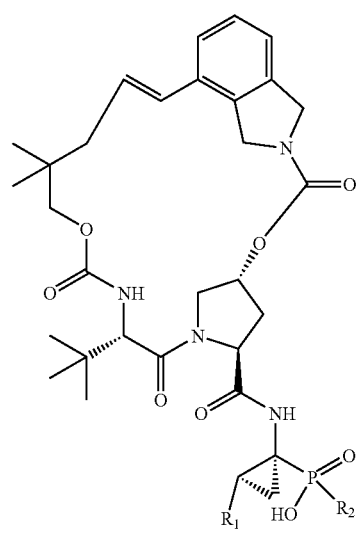
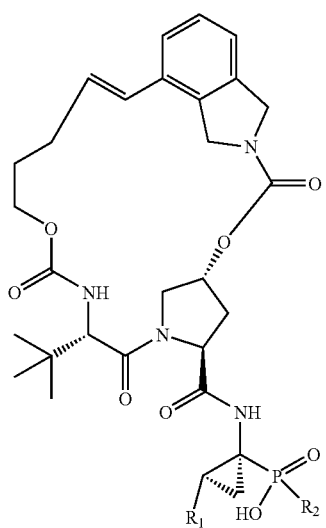

-continued
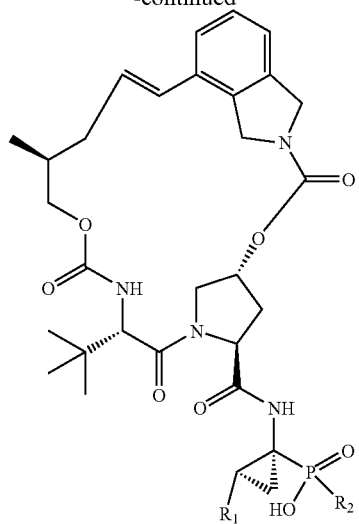
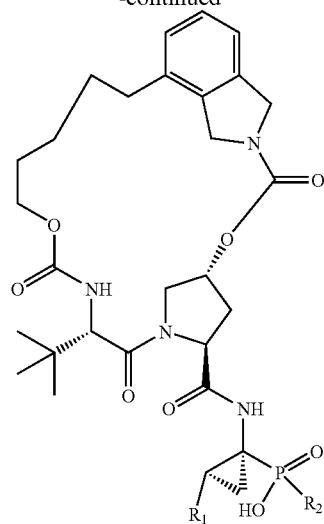
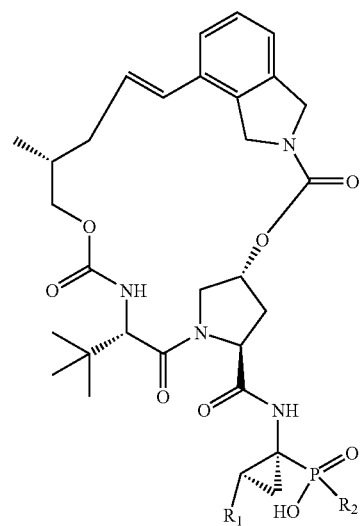
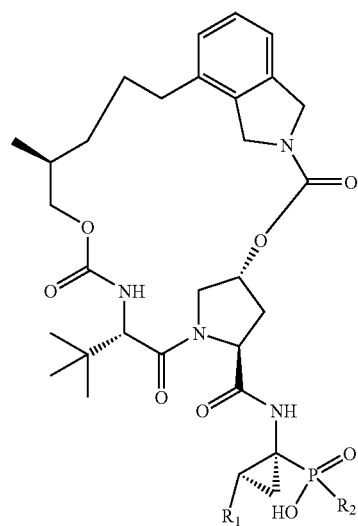
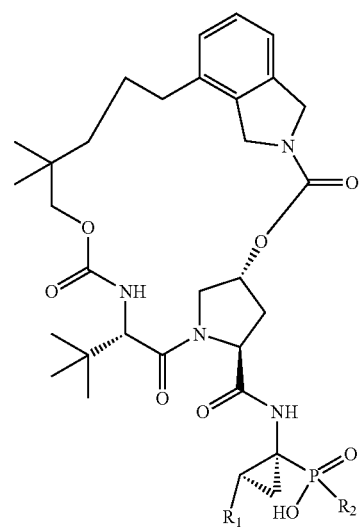
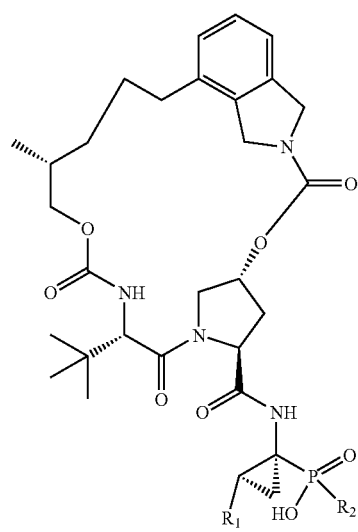

-continued
67
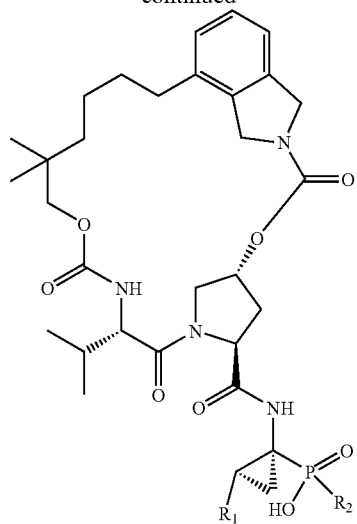
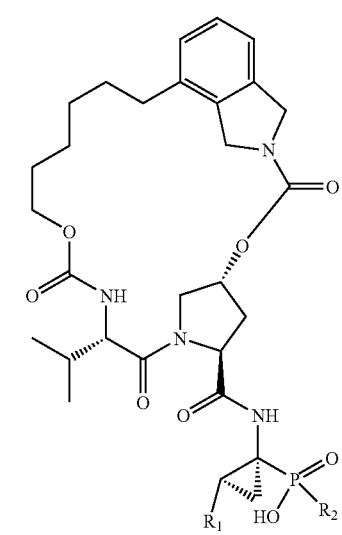
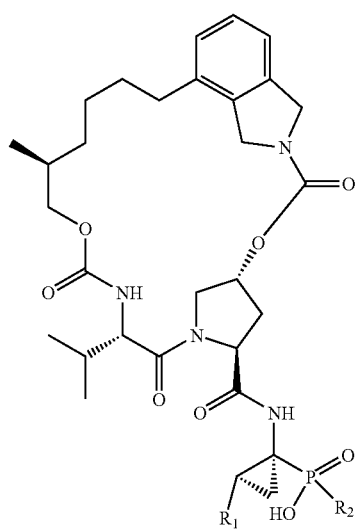
-continued
68
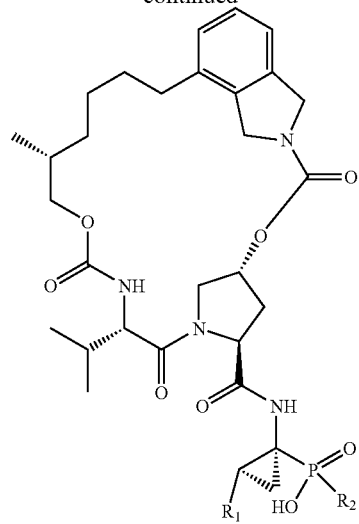
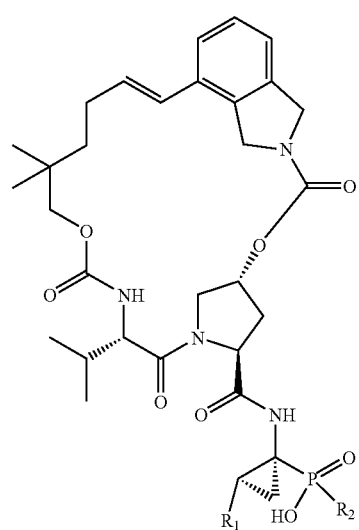
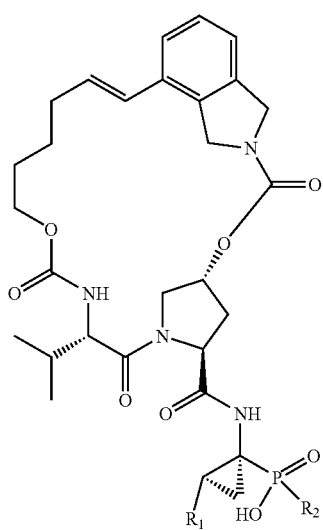

69
-continued
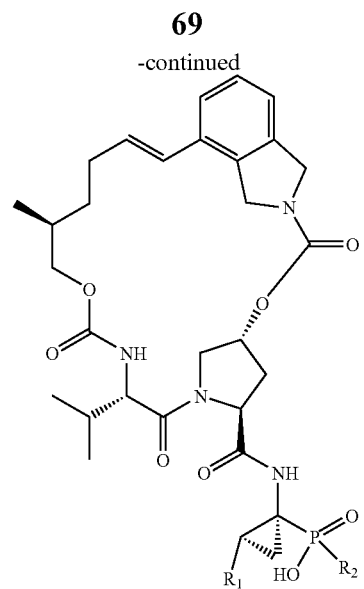
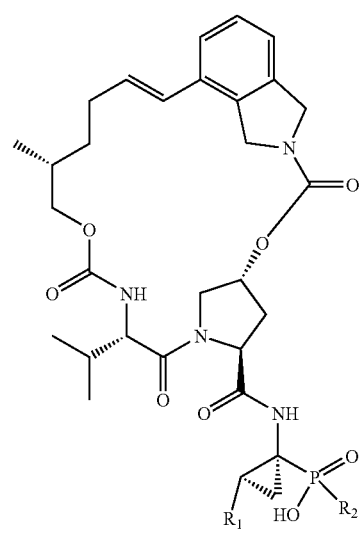
70
-continued
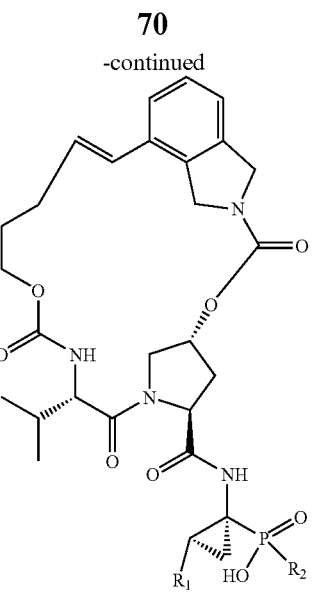
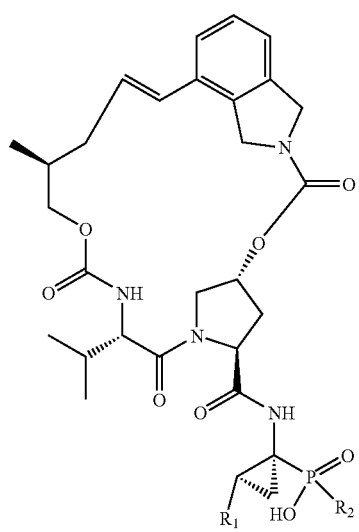
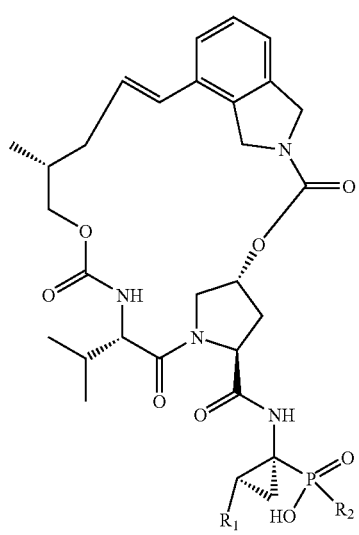

| 71 | 72 |
|---|---|
| -continued | -continued |
| 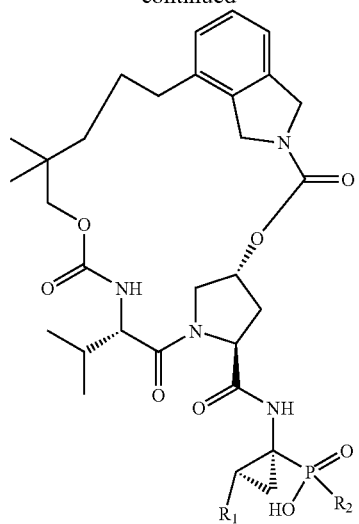 | 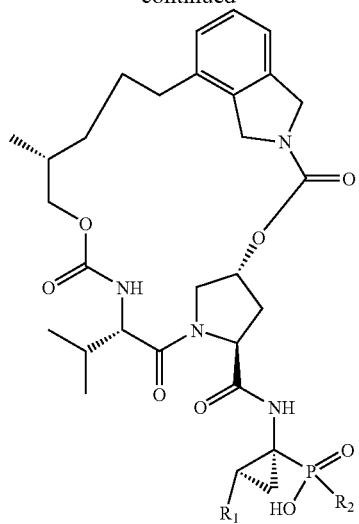 |
| 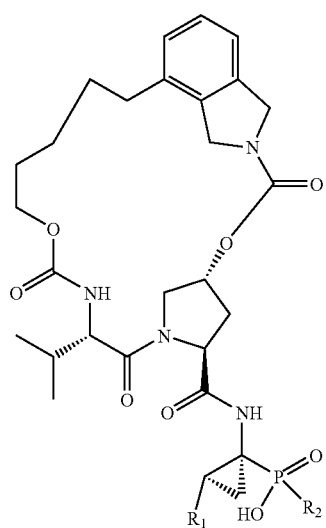 | 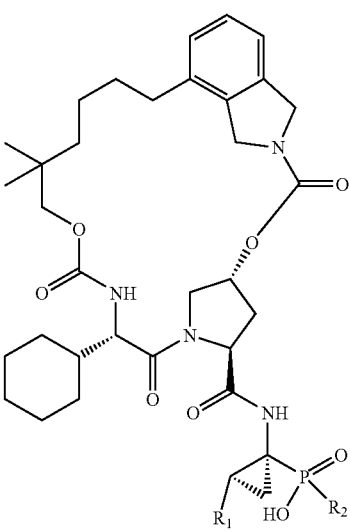 |
| 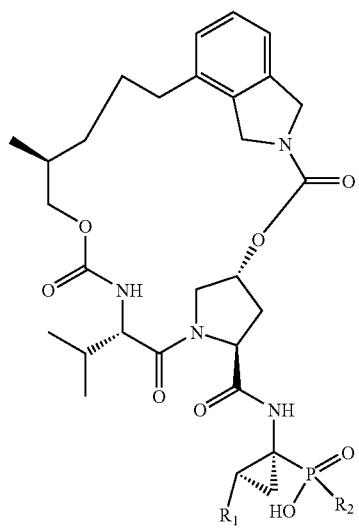 | 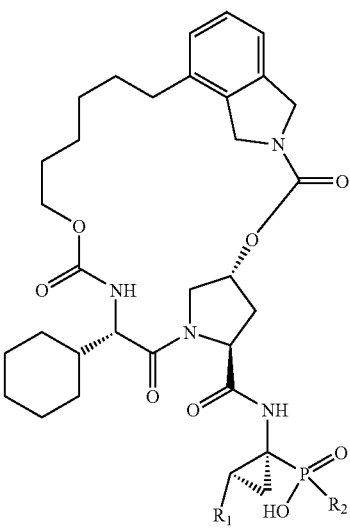 |

73
-continued
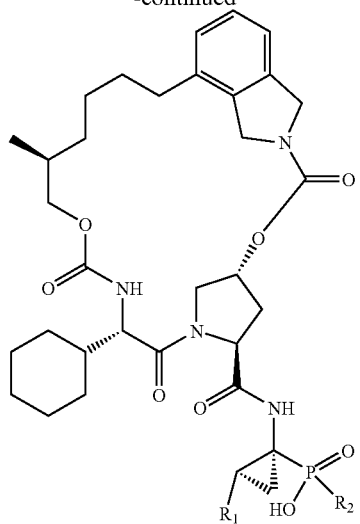
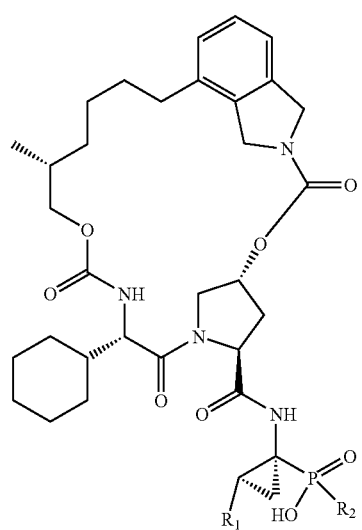
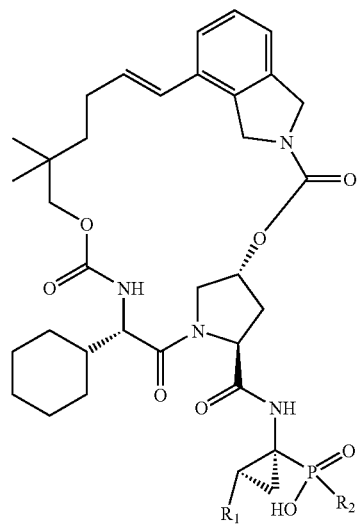
74
-continued
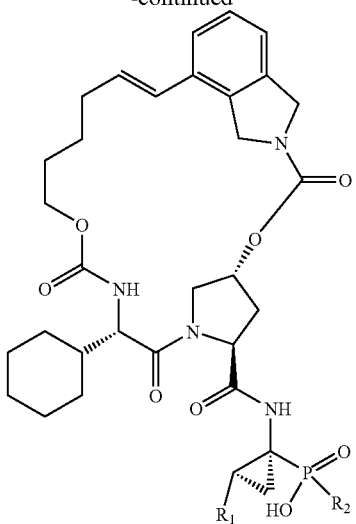
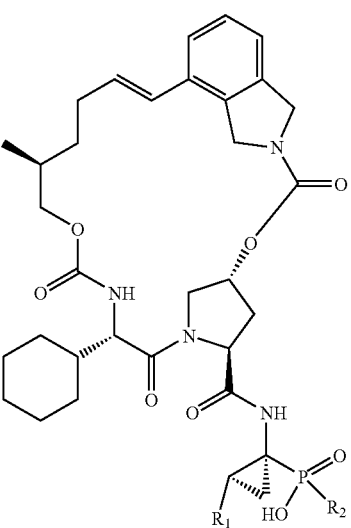
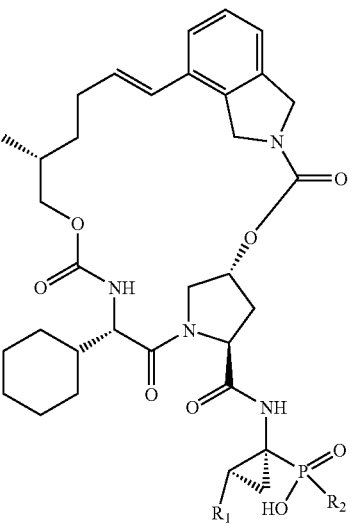

75
-continued
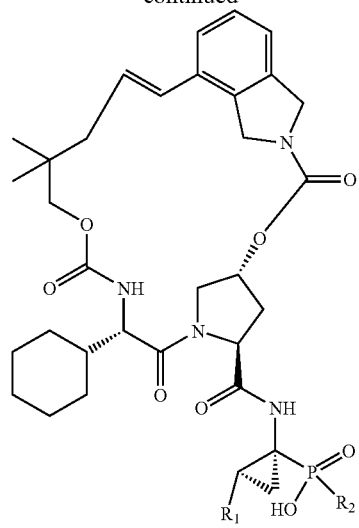
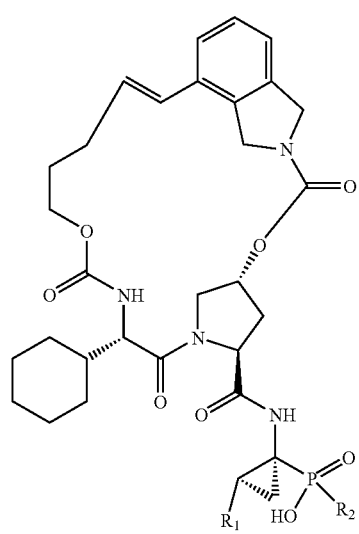
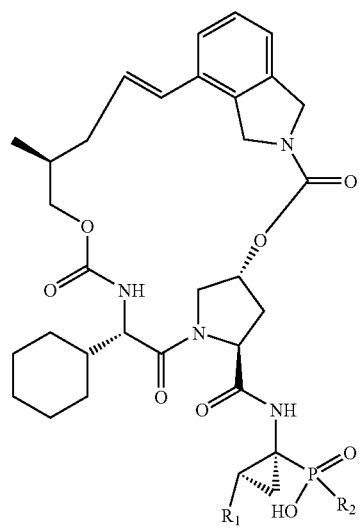
76
-continued
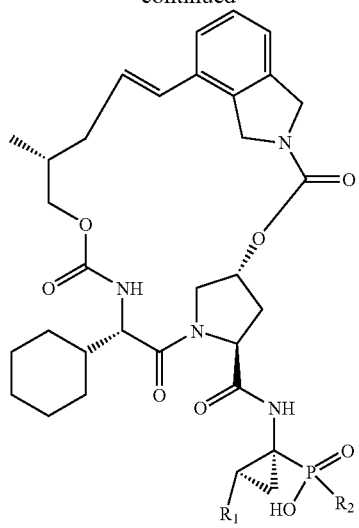
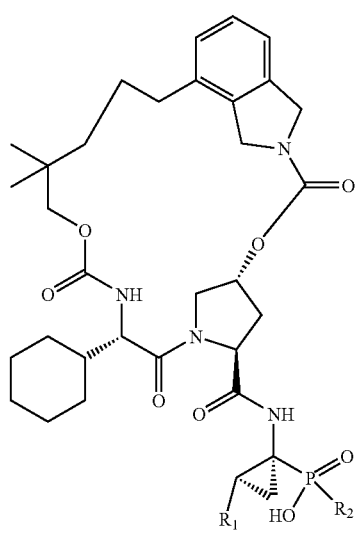
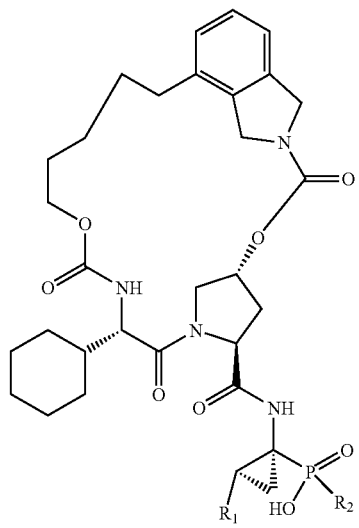

77
-continued
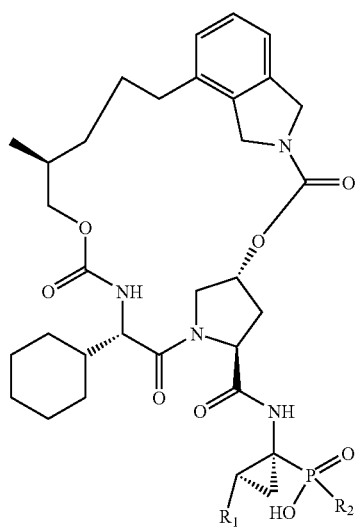
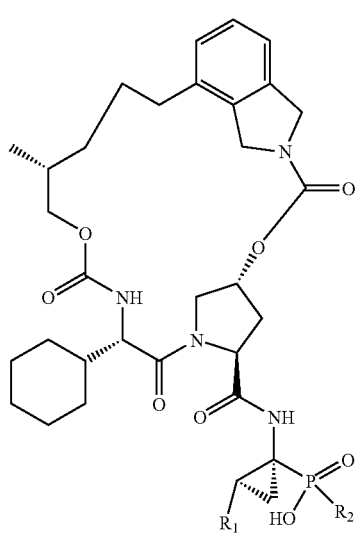
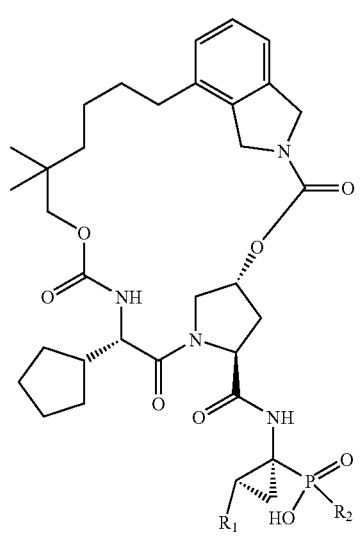
78
-continued
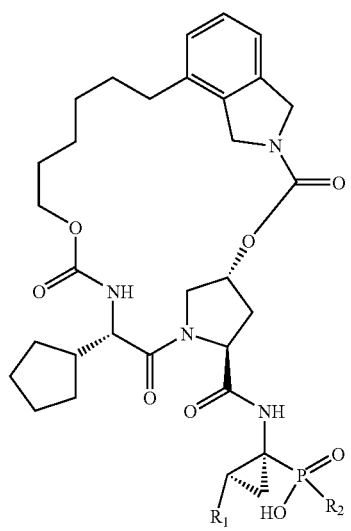
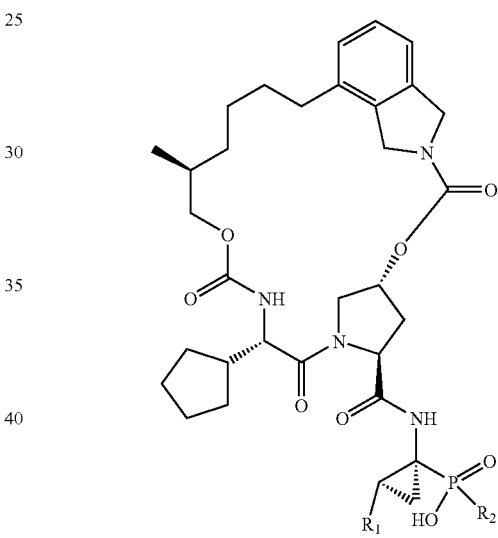
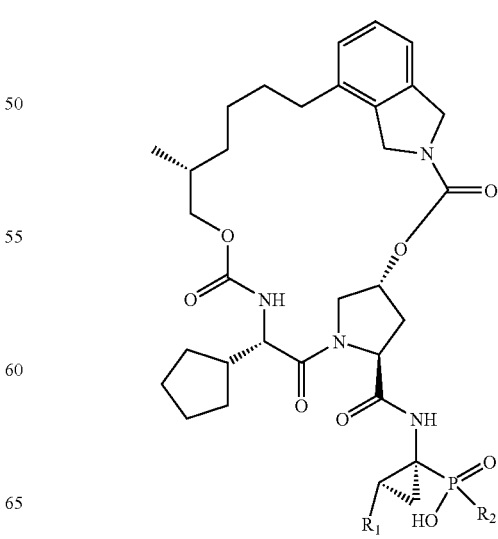

79
-continued
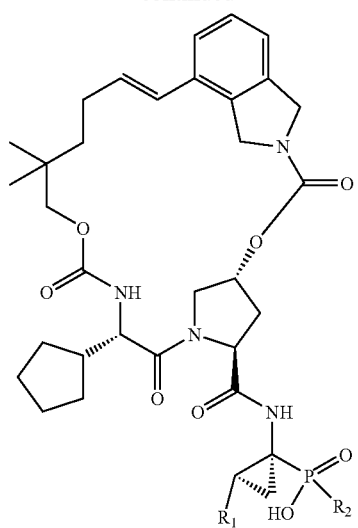
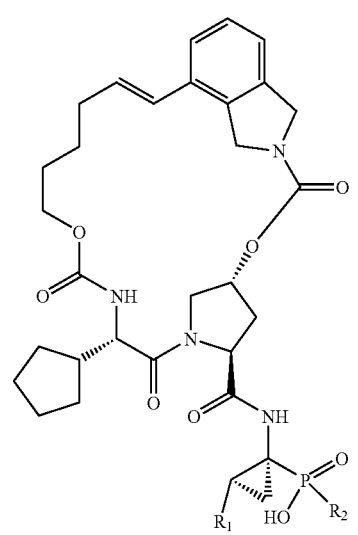
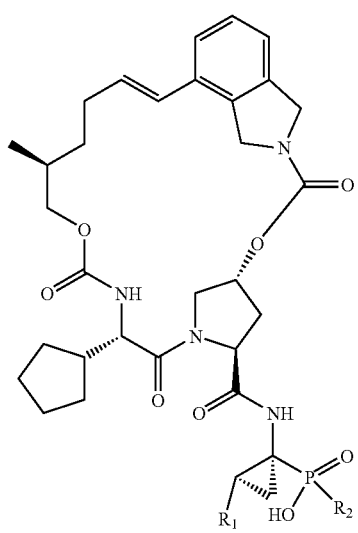
80
-continued
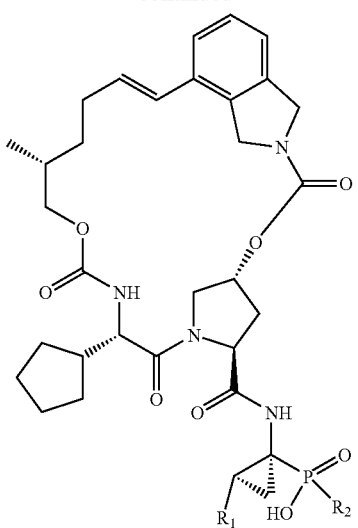
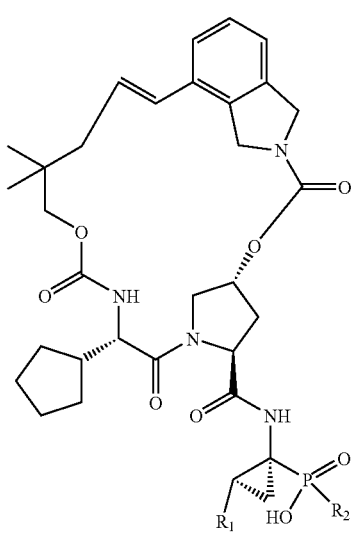
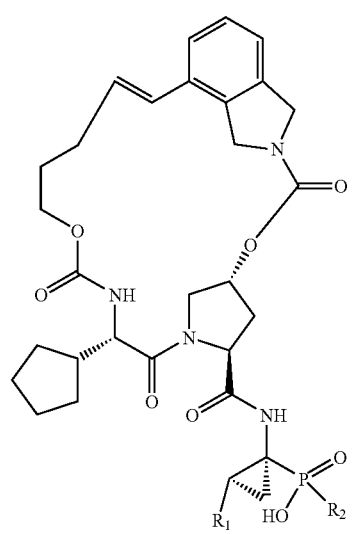

81
-continued
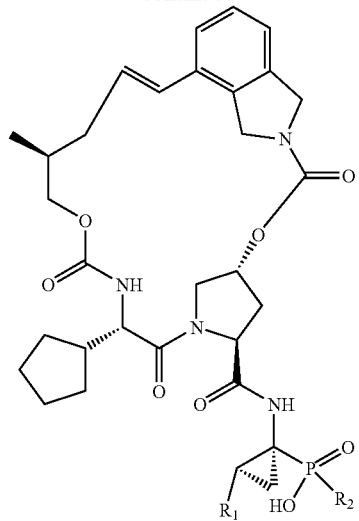
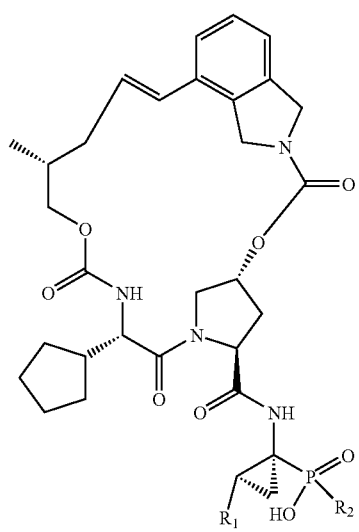
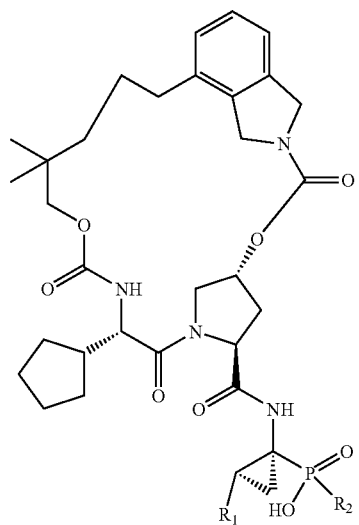
82
-continued
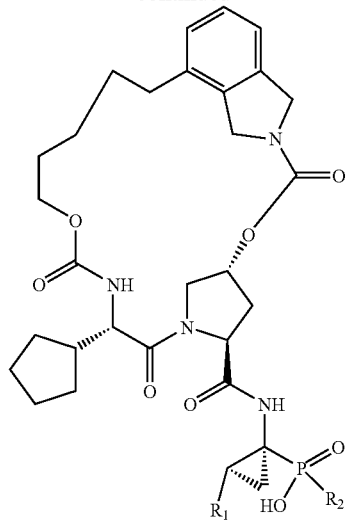
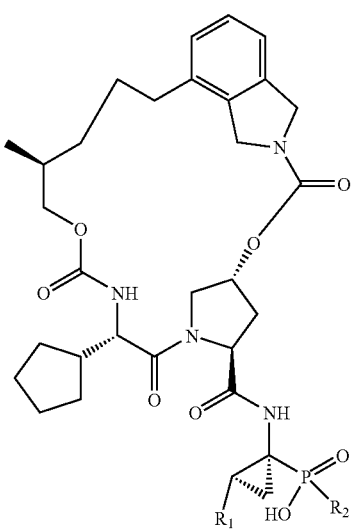
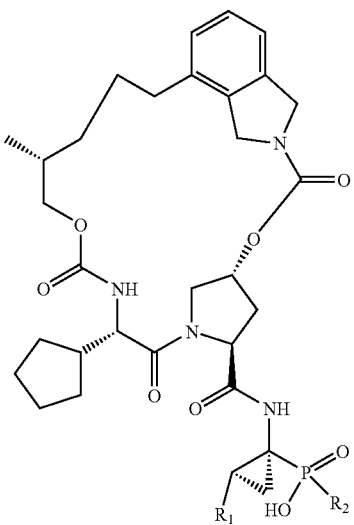

83
-continued
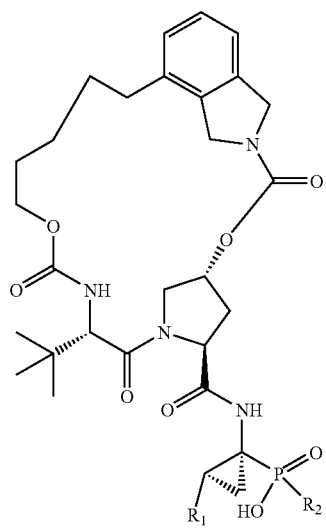
84
-continued
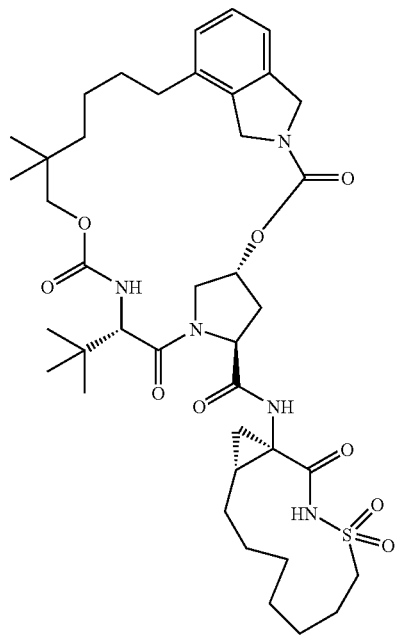
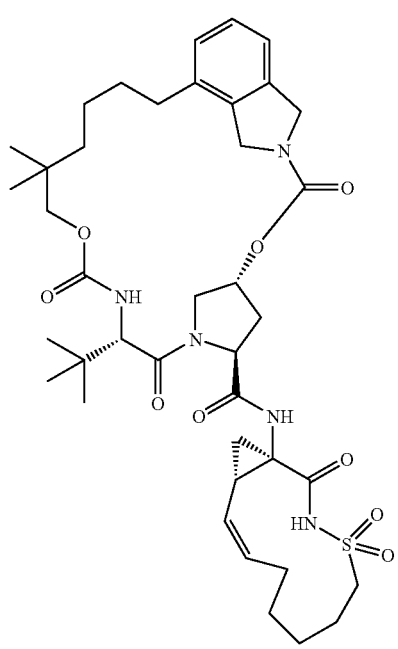
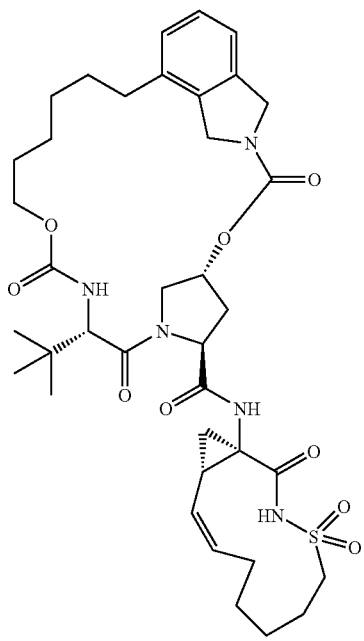

85
-continued
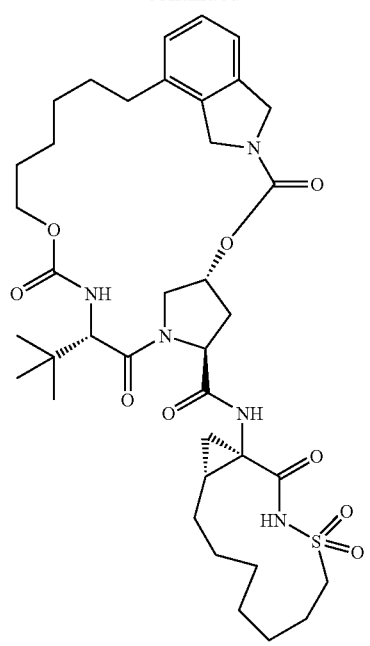
86
-continued
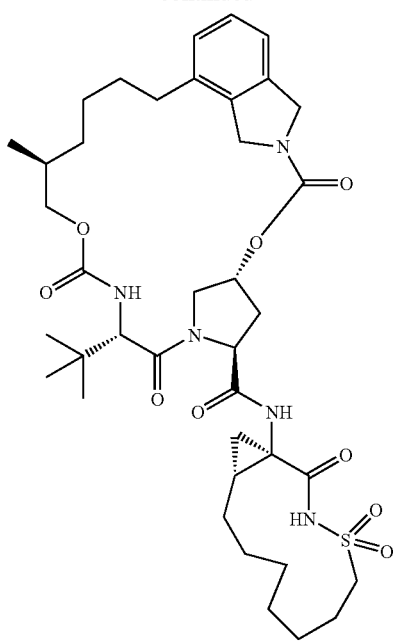
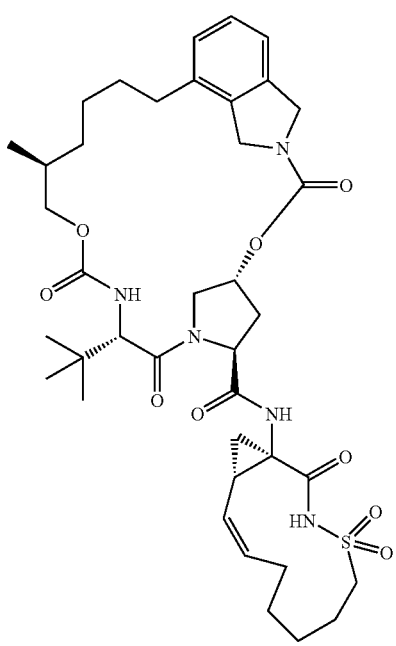
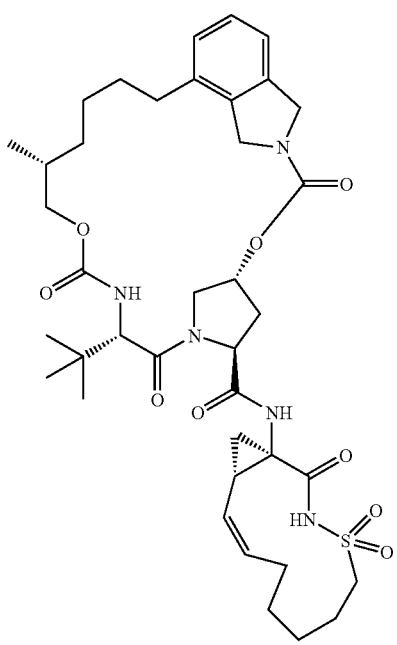

-continued

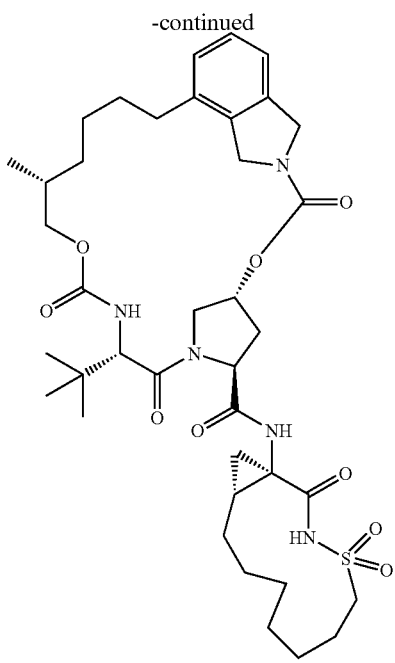

What is claimed is:
1. A compound of formula (I):

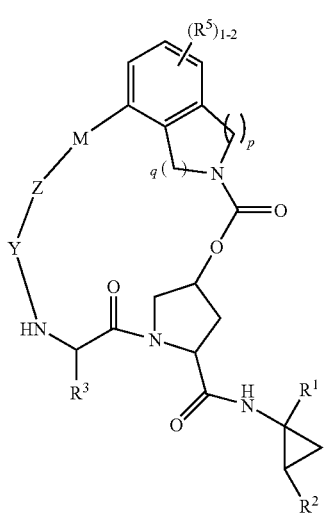

and/or a pharmaceutically acceptable salt or hydrate thereof, wherein:
p and q are independently 1 or 2;
$R^1$ and $R^2$, together with the cyclopropyl ring to which they are attached, form the following bicyclic ring system:

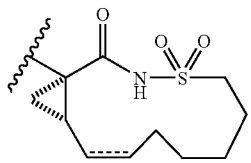

wherein

----- is a single or double bond;
$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —$C(O)R^{10}$, and —$CON(R^{10})_2$;
Het is a 5- to 6-membered saturated cyclic ring having 1 or 2 heteroatoms selected from N, O and S, wherein said ring is optionally substituted with 1 to 3 substituents selected from halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —$C(O)R^{10}$, and —$CON(R^{10})_2$;
$R^4$ is H, $C_1$-$C_8$ alkyl, $C_3$-$C_8$ cycloalkyl($C_1$-$C_8$)alkyl, or aryl ($C_1$-$C_8$)alkyl; wherein aryl is phenyl or naphthyl and said alkyl, cycloalkyl, or aryl is optionally substituted with 1 to 3 substituents selected from the group consisting of halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo ($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —$C(O)R^{10}$, and —$CON(R^{10})_2$;
$R^5$ is H, halo, —$OR^{10}$, $C_1$-$C_6$ alkyl, —CN, —$CF_3$, —$SR^{10}$, —$SO_2(C_1$-$C_6$ alkyl), $C_3$-$C_8$ cycloalkyl, $C_3$-$C_8$ cycloalkoxy, $C_1$-$C_6$ haloalkyl, —$N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo ($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N$ $(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;
$R^6$ is $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl ($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents or aryl is substituted by P(O)R$^{11}$R$^{12}$; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is —C(=O)—, —SO$_2$—, or —C(=N—CN)—;

Z is —C(R$^{10}$)$_2$—, —O—, or —N(R$^4$)—;

M is C$_1$-C$_{12}$ alkylene or C$_2$-C$_{12}$ alkenylene, wherein said alkylene or alkenylene is optionally substituted with 1 or 2 substituents selected from the group consisting of C$_1$-C$_8$ alkyl, C$_3$-C$_8$ cycloalkyl(C$_1$-C$_8$ alkyl), and aryl (C$_1$-C$_8$ alkyl); and the 2 adjacent substituents of M are optionally taken together to form a 3- to 6-membered cyclic ring containing 0 to 3 heteroatoms selected from N, O and S;

each R$^7$ is independently H, C$_1$-C$_6$ alkyl, C$_3$-C$_6$ cycloalkyl, C$_3$-C$_6$ cycloalkyl(C$_1$-C$_5$)alkyl, aryl, aryl(C$_1$-C$_4$)alkyl, heteroaryl, heteroaryl(C$_1$-C$_4$ alkyl), heterocyclyl, or heterocyclyl(C$_1$-C$_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, —OR$^{10}$, C$_1$-C$_6$ alkyl, —CN, —CF$_3$, —NO$_2$, —SR$^{10}$, —CO$_2$R$^{10}$, —CON(R$^{10}$)$_2$, —C(O)R$^{10}$, —N(R$^{10}$)C(O)R$^{10}$, —SO$_2$(C$_1$-C$_6$ alkyl), —S(O)(C$_1$-C$_6$ alkyl), C$_3$-C$_8$ cycloalkyl, C$_3$-C$_8$ cycloalkoxy, C$_1$-C$_6$ haloalkyl, —N(R$^{10}$)$_2$, —N(C$_1$-C$_6$ alkyl)O(C$_1$-C$_6$ alkyl), halo(C$_1$-C$_6$ alkoxy), —NR$^{10}$SO$_2$R$^{10}$, —SO$_2$N(R$^{10}$)$_2$, —NHCOOR$^{10}$, —NHCONHR$^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

each R$^{10}$ is independently H or C$_1$-C$_6$ alkyl;

each R$^{11}$ is independently C$_1$-C$_6$ alkyl, C$_1$-C$_4$ alkenyl, —OR$^{13}$, —N(R$^{10}$)—V—CO$_2$R$^{10}$, —O—V—CO$_2$R$^{10}$, —S—V—CO$_2$R$^{10}$, —N(R$^{10}$)(R$^{13}$), R$^{14}$, or —N(R$^{10}$)SO$_2$R$^6$;

each R$^{12}$ is independently —OR$^{13}$, —N(R$^{10}$)—V—CO$_2$R$^{10}$, —O—V—CO$_2$R$^{10}$, —S—V—CO$_2$R$^{10}$, or —N(R$^{10}$)(R$^{13}$);

or R$^{11}$ and R$^{12}$ are optionally taken together, with the phosphorus atom to which they are attached, to form a 5- to 7-membered monocyclic ring;

each V is independently —CH(R$^{15}$) or C$_1$-C$_4$ alkylene-CH(R$^{15}$);

each R$^{13}$ is independently H, C$_1$-C$_6$ alkyl, C$_2$-C$_6$ alkenyl, C$_3$-C$_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl (C$_1$-C$_4$ alkyl), C$_3$-C$_8$ cycloalkyl, C$_3$-C$_8$ cycloalkyl(C$_1$-C$_4$ alkyl), heteroaryl, heteroaryl(C$_1$-C$_4$ alkyl), heterocyclyl, heterocyclyl(C$_1$-C$_4$ alkyl), C$_1$-C$_6$ alkyl, halo, —OC(O)OR$^6$, —OC(O)R$^6$, —OR$^{10}$, —SR$^{10}$, —N(R$^{10}$)$_2$, —C(O)R$^{10}$, —NO$_2$, —CN, —CF$_3$, —SO$_2$(C$_1$-C$_6$ alkyl), —S(O)(C$_1$-C$_6$ alkyl), —NR$^{10}$SO$_2$R$^6$, —SO$_2$N(R$^6$)$_2$, —NHCOOR$^6$, —NHCOR$^6$, —NHCONHR$^6$, —CO$_2$R$^{10}$, and —C(O)N(R10)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

R$^{14}$ is C$_1$-C$_6$ alkyl, C$_2$-C$_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of C$_1$-C$_6$ alkyl, halo, —OC(O)OR$^6$, —OC(O)R$^6$, —OR$^{10}$, —SR$^{10}$, —N(R$^{10}$)$_2$, —C(O)R$^{10}$, —NO$_2$, —CN, —CF$_3$, —SO$_2$(C$_1$-C$_6$ alkyl), —S(O)(C$_1$-C$_6$ alkyl), —NR$^{10}$SO$_2$R$^6$, —SO$_2$N(R$^6$)$_2$, —NHCOOR$^6$, —NHCOR$^6$, —NHCONHR$^6$, —CO$_2$R$^{10}$, and —C(O)N(R$^{10}$)$_2$; and each R$^{15}$ is independently C$_1$-C$_6$ alkyl, C$_2$-C$_6$ alkenyl, C$_3$-C$_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of C$_1$-C$_6$ alkyl, halo, —OC(O)OR$^6$, —OC(O)R$^6$, —OR$^{10}$, —SR$^{10}$, —N(R$^{10}$)$_2$, —C(O)R$^{10}$, —NO$_2$, —CN, —CF$_3$, —SO$_2$(C$_1$-C$_6$ alkyl), —S(O)(C$_1$-C$_6$ alkyl), —NR$^{10}$SO$_2$R$^6$, —SO$_2$N(R$^6$)$_2$, —NHCOOR$^6$, —NHCOR$^6$, —NHCONHR$^6$, —CO$_2$R$^{10}$, and —C(O)N(R$^{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

2. A compound of claim 1, wherein p and q are 1.

3. A compound of claim 1, wherein R$^{11}$ is Independently C$_1$-C$_6$ alkyl, C$_1$-C$_4$ alkenyl, or —OR$^{13}$, and R$^{12}$ is independently —OR$^{13}$.

4. A compound of claim 3, wherein R$^{13}$ is H or C$_1$-C$_6$ alkyl.

5. A compound of claim 3, wherein R$^{11}$ is selected from the group consisting of —OCH$_2$CH$_3$, —CH$_2$CH$_3$, —CH$_3$, —CH(CH$_3$)$_2$, phenyl, —CH=CH$_2$, —OH, —CH$_2$CH$_2$CH$_3$, and —CH$_2$CH$_2$CH$_2$CH$_3$, and R$^{12}$ is —OH or —OCH$_2$CH$_3$.

6. A compound of claim 1, wherein $R^3$ is $C_1$-$C_8$ alkyl or $C_3$-$C_8$ cycloalkyl.

7. A compound of claim 6, wherein $R^3$ is —C(CH$_3$)$_3$, cyclohexyl or cyclopentyl.

8. A compound of claim 1, wherein $R^5$ is H.

9. A compound of claim 1, wherein Z is —O—.

10. A compound of claim 1, wherein Y is —C(=O)—.

11. A compound of claim 1, wherein M is M is $C_1$-$C_{12}$ alkylene or $C_2$-$C_{12}$ alkenylene, wherein said alkylene or alkenylene is optionally substituted with 1 or 2 substituents selected from the group consisting of $C_1$-$C_8$ alkyl.

12. A compound of claim 11, wherein M is selected from the group consisting of —(CH$_2$)$_4$C(CH$_3$)$_2$(CH$_2$)—, —(CH$_2$)$_6$—, —(CH$_2$)$_4$CH(CH$_3$)CH$_2$—, —CH=CH(CH$_2$)$_2$C(CH$_3$)$_2$ CH$_2$—, —CH=CH(CH$_2$)$_2$CH(CH$_3$)CH$_2$—, —CH=CHCH$_2$C(CH$_3$)$_2$CH$_2$—, —CH=CH(CH$_2$)$_3$—, —CH=CH(CH$_2$)$_4$—, —CH=CHCH$_2$CH(CH$_3$)CH$_2$—, —(CH$_2$)$_3$C(CH$_3$)$_2$CH$_2$—, —(CH$_2$)$_5$—, and —(CH$_2$)$_3$CH(CH$_3$)CH$_2$—.

13. A pharmaceutical composition comprising an effective amount of a compound of claim 1, and a pharmaceutically acceptable carrier.

14. A pharmaceutical composition of claim 13, further comprising a second therapeutic agent selected from the group consisting of a HCV antiviral agent, an immunomodulator, and an anti-infective agent.

15. A method of treating HCV infection comprising administering to a patient in need thereof a composition comprising a compound of formula (I):

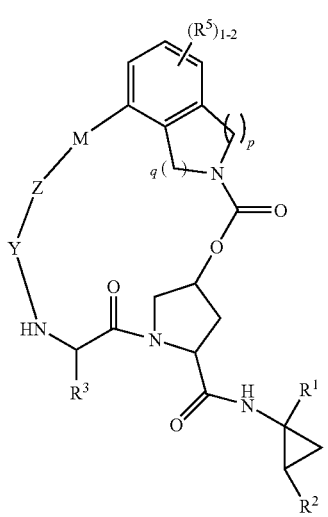

and/or a pharmaceutically acceptable salt or hydrate thereof, wherein:

p and q are independently 1 or 2;

$R^1$ and $R^2$, together with the cyclopropyl ring to which they are attached, form the following bicyclic ring system:

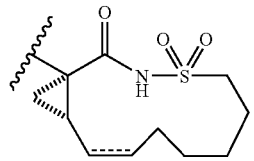

wherein

----- is a single or double bond;

$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, —OR$^{10}$, —SR$^{10}$, —N(R$^{10}$)$_2$, —N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), —NO$_2$, —CN, —CF$_3$, —SO$_2$(C$_1$-C$_6$ alkyl), —S(O)(C$_1$-C$_6$ alkyl), —NR$^{10}$SO$_2$R$^6$—SO$_2$N(R$^6$)$_2$, —NHCOOR$^6$, —NHCOR$^6$, —NHCONHR$^6$, —CO$_2$R$^{10}$, —C(O)R$^{10}$, and —CON(R$^{10}$)$_2$;

Het is a 5- to 6-membered saturated cyclic ring having 1 or 2 heteroatoms selected from N, O and S, wherein said ring is optionally substituted with 1 to 3 substituents selected from halo, —OR$^{10}$, —SR$^{10}$, —N(R$^{10}$)$_2$, —N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), —NO$_2$, —CN, —CF$_3$, —SO$_2$(C$_1$-C$_6$ alkyl), —S(O)(C$_1$-C$_6$ alkyl), —NR$^{10}$SO$_2$R$^6$—SO$_2$N(R$^6$)$_2$, —NHCOOR$^6$, —NHCOR$^6$, —NHCONHR$^6$, —CO$_2$R$^{10}$, —C(O)R$^{10}$, and —CON(R$^{10}$)$_2$;

$R^4$ is H, C$_1$-C$_8$ alkyl, C$_3$-C$_8$ cycloalkyl(C$_1$-C$_8$)alkyl, or aryl (C$_1$-C$_8$)alkyl; wherein aryl is phenyl or naphthyl and said alkyl, cycloalkyl, or aryl is optionally substituted with 1 to 3 substituents selected from the group consisting of halo, —OR$^{10}$, —SR$^{10}$, —N(R$^{10}$)$_2$, —N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), —NO$_2$, —CN, —CF$_3$, —SO$_2$(C$_1$-C$_6$ alkyl), —S(O)(C$_1$-C$_6$ alkyl), —NR$^{10}$SO$_2$R$^6$, —SO$_2$N(R$^6$)$_2$, —NHCOOR$^6$, —NHCOR$^6$, —NHCONHR$^6$, —CO$_2$R$^{10}$, —C(O)R$^{10}$, and —CON(R$^{10}$)$_2$;

$R^5$ is H, halo, —OR$^{10}$, C$_1$-C$_6$ alkyl, —CN, —CF$_3$, —SR$^{10}$, —SO$_2$(C$_1$-C$_6$ alkyl), C$_3$-C$_8$ cycloalkyl, C$_3$-C$_8$ cycloalkoxy, C$_1$-C$_6$ haloalkyl, —N(R$^7$)$_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, OR$^{10}$, SR$^{10}$, N(R$^7$)$_2$, N(C$_1$-C$_6$ alkyl)O(C$_1$-C$_6$ alkyl), C$_1$-C$_6$ alkyl, C$_1$-C$_6$ haloalkyl, halo (C$_1$-C$_6$ alkoxy), C$_3$-C$_6$ cycloalkyl, C$_3$-C$_6$ cycloalkoxy, NO$_2$ CN, CF$_3$, SO$_2$(C$_1$-C$_6$ alkyl), NR$^{10}$SO$_2$R$^6$, SO$_2$N (R$^6$)$_2$, S(O)(C$_1$-C$_6$ alkyl), NHCOOR$^6$, NHCOR$^6$, NHCONHR$^6$, CO$_2$R$^{10}$, C(O)R$^{10}$, and)CON(R$^{10}$)$_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^6$ is C$_1$-C$_6$ alkyl, C$_3$-C$_6$ cycloalkyl, C$_3$-C$_6$ cycloalkyl(C$_1$-C$_5$)alkyl, aryl, aryl(C$_1$-C$_4$)alkyl, heteroaryl, heteroaryl (C$_1$-C$_4$ alkyl), heterocyclyl, or heterocyclyl(C$_1$-C$_8$ alkyl), wherein said alkyl, cycloalkyl, aryl, heteroaryl, or heterocyclyl is optionally substituted with 1 to 2 W substituents or aryl is substituted by $P(O)R^{11}R^{12}$; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is —C(=O)—, —SO$_2$—, or —C(=N—CN)—;

Z is —C(R$^{10}$)$_2$—, —O—, or —N(R$^4$)—;

M is $C_1$-$C_{12}$ alkylene or $C_2$-$C_{12}$ alkenylene, wherein said alkylene or alkenylene is optionally substituted with 1 or 2 substituents selected from the group consisting of $C_1$-$C_8$ alkyl, $C_3$-$C_8$ cycloalkyl($C_1$-$C_8$ alkyl), and aryl ($C_1$-$C_8$ alkyl); and the 2 adjacent substituents of M are optionally taken together to form a 3- to 6-membered cyclic ring containing 0 to 3 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, —OR$^{10}$, $C_1$-$C_6$ alkyl, —CN, —CF$_3$, —NO$_2$, —SR$^{10}$, —CO$_2$R$^{10}$, —CON(R$^{10}$)$_2$, —C(O)R$^{10}$, —N(R$^{10}$)C(O)R$^{10}$, —SO$_2$($C_1$-$C_6$ alkyl), —S(O)($C_1$-$C_6$ alkyl), $C_3$-$C_8$ cycloalkyl, $C_3$-$C_8$ cycloalkoxy, $C_1$-$C_6$ haloalkyl, —N(R$^{10}$)$_2$, —N($C_1$-$C_6$ alkyl)O($C_1$-$C_6$ alkyl), halo($C_1$-$C_6$ alkoxy), —NR$^{10}$SO$_2$R$^{10}$, —SO$_2$N(R$^{10}$)$_2$, —NHCOOR$^{10}$, —NHCONHR$^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

each $R^{10}$ is independently H or $C_1$-$C_6$ alkyl;

each $R^{11}$ is independently $C_1$-$C_6$ alkyl, $C_1$-$C_4$ alkenyl, —OR$^{13}$, —N(R$^{10}$)—V—CO$_2$R$^{10}$, —O—V—CO$_2$R$^{10}$, —S—V—CO$_2$R$^{10}$, —N(R$^{10}$)(R$^{13}$), R$^{14}$, or —N(R$^{10}$)SO$_2$R$^6$;

each $R^{12}$ is independently —OR$^{13}$, —N(R$^{10}$)—V—CO$_2$R$^{10}$, —O—V—CO$_2$R$^{10}$, —S—V—CO$_2$R$^{10}$, or —N(R$^{10}$)(R$^{13}$);

or $R^{11}$ and $R^{12}$ are optionally taken together, with the phosphorus atom to which they are attached, to form a 5- to 7-membered monocyclic ring;

each V is independently —CH(R$^{15}$) or $C_1$-$C_4$ alkylene-CH(R$^{15}$);

each $R^{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl ($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, —OC(O)OR$^6$, —OC(O)R$^6$, —OR$^{10}$, —SR$^{10}$, —N(R$^{10}$)$_2$, —C(O)R$^{10}$, —NO$_2$, —CN, —CF$_3$, —SO$_2$($C_1$-$C_6$ alkyl), —S(O)($C_1$-$C_6$ alkyl), —NR$^{10}$SO$_2$R$^6$, —SO$_2$N(R$^6$)$_2$, —NHCOOR$^6$, —NHCOR$^6$, —NHCONHR$^6$, —CO$_2$R$^{10}$, and —C(O)N(R10)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of $C_1$-$C_6$ alkyl, halo, —OC(O)OR$^6$, —OC(O)R$^6$, —OR$^{10}$, —SR$^{10}$, —N(R$^{10}$)$_2$, —C(O)R$^{10}$, —NO$_2$, —CN, —CF$_3$, —SO$_2$($C_1$-$C_6$ alkyl), —S(O)($C_1$-$C_6$ alkyl), —NR$^{10}$SO$_2$R$^6$—SO$_2$N(R$^6$)$_2$, —NHCOOR$^6$, —NHCOR$^6$, —NHCONHR$^6$, —CO$_2$R$^{10}$, and —C(O)N(R$^{10}$)$_2$; and each $R^{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of $C_1$-$C_6$ alkyl, halo, —OC(O)OR$^6$, —OC(O)R$^6$, —OR$^{10}$, —SR$^{10}$, —N(R$^{10}$)$_2$, —C(O)R$^{10}$, —NO$_2$, —CN, —CF$_3$, —SO$_2$($C_1$-$C_6$ alkyl), —S(O)($C_1$-$C_6$ alkyl), —NR$^{10}$SO$_2$R$^6$, —SO$_2$N(R$^6$)$_2$, —NHCOOR$^6$, —NHCOR$^6$, —NHCONHR$^6$, —CO$_2$R$^{10}$, and —C(O)N(R$^{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

16. A method of inhibiting HCV NS3 protease in a subject in need thereof, said method comprising administering to the subject an effective amount of a compound of formula (I):

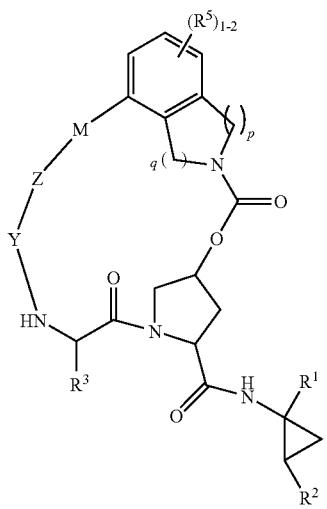

and/or a pharmaceutically acceptable salt or hydrate thereof, wherein:

p and q are independently 1 or 2;

$R^1$ and $R^2$, together with the cyclopropyl ring to which they are attached, form the following bicyclic ring system:

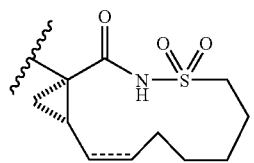

wherein

----- is a single or double bond;

$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is optionally substituted with 1 to 3 substituents selected from the group consisting of halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —$C(O)R^{10}$, and —$CON(R^{10})_2$;

Het is a 5- to 6-membered saturated cyclic ring having 1 or 2 heteroatoms selected from N, O and S, wherein said ring is optionally substituted with 1 to 3 substituents selected from halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —$C(O)R^{10}$, and —$CON(R^{10})_2$;

$R^4$ is H, $C_1$-$C_8$ alkyl, $C_3$-$C_8$ cycloalkyl($C_1$-$C_8$)alkyl, or aryl($C_1$-$C_8$)alkyl; wherein aryl is phenyl or naphthyl and said alkyl, cycloalkyl, or aryl is optionally substituted with 1 to 3 substituents selected from the group consisting of halo, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, —$C(O)R^{10}$, and —$CON(R_{10})_2$;

$R^5$ is H, halo, —$OR^{10}$, $C_1$-$C_6$ alkyl, —CN, —$CF_3$, —$SR^{10}$, —$SO_2(C_1$-$C_6$ alkyl), $C_3$-$C_8$ cycloalkyl, $C_3$-$C_8$ cycloalkoxy, $C_1$-$C_6$ haloalkyl, —$N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^6$ is $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents or aryl is substituted by $P(O)R^{11}R^{12}$; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is —C(=O)—, —$SO_2$—, or —C(=N—CN)—;

Z is —$C(R^{10})_2$—, —O—, or —$N(R^4)$—;

M is $C_1$-$C_{12}$ alkylene or $C_2$-$C_{12}$ alkenylene, wherein said alkylene or alkenylene is optionally substituted with 1 or 2 substituents selected from the group consisting of $C_1$-$C_8$ alkyl, $C_3$-$C_8$ cycloalkyl($C_1$-$C_8$ alkyl), and aryl ($C_1$-$C_8$ alkyl); and the 2 adjacent substituents of M are optionally taken together to form a 3- to 6-membered cyclic ring containing 0 to 3 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, $-OR^{10}$, $C_1$-$C_6$ alkyl, $-CN$, $-CF_3$, $-NO_2$, $-SR^{10}$, $-CO_2R^{10}$, $-CON(R^{10})_2$, $-C(O)R^{10}$, $-N(R^{10})C(O)R^{10}$, $-SO_2(C_1$-$C_6$ alkyl), $-S(O)(C_1$-$C_6$ alkyl), $C_3$-$C_8$ cycloalkyl, $C_3$-$C_8$ cycloalkoxy, $C_1$-$C_6$ haloalkyl, $-N(R^{10})_2$, $-N(C_1$-$C_6$ alkyl)$O(C_1$-$C_6$ alkyl), halo($C_1$-$C_6$ alkoxy), $-NR^{10}SO_2R^{10}$, $-SO_2N(R^{10})_2$, $-NHCOOR^{10}$, $-NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

each $R^{10}$ is independently H or $C_1$-$C_6$ alkyl;

each $R^{11}$ is independently $C_1$-$C_6$ alkyl, $C_1$-$C_4$ alkenyl, $-OR^{13}$,) $-N(R^{10})-V-CO_2R^{10}$, $-O-V-CO_2R^{10}$, $-S-V-CO_2R^{10}$, $-N(R^{10})(R^{13})$, $R^{14}$, or $-N(R^{10})SO_2R^6$;

each $R^{12}$ is independently $-OR^{13}$, $-NR^{10}-V-CO_2R^{10}$, $-O-V-CO_2R^{10}$, $-S-V-CO_2R^{10}$, or $-N(R^{10})(R^{13})$;

or $R^{11}$ and $R^{12}$ are optionally taken together, with the phosphorus atom to which they are attached, to form a 5- to 7-membered monocyclic ring;

each V is independently $-CH(R^{15})$ or $C_1$-$C_4$ alkylene-CH($R^{15}$);

each $R^{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl ($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, $-OC(O)OR^6$, $-OC(O)R^6$, $-OR^{10}$, $-SR^{10}$, $-N(R^{10})_2$, $-C(O)R^{10}$, $-NO_2$, $-CN$, $-CF_3$, $-SO_2(C_1$-$C_6$ alkyl), $-S(O)(C_1$-$C_6$ alkyl), $-NR^{10}SO_2R^6$, $-SO_2N(R^6)_2$, $-NHCOOR^6$, $-NHCOR^6$, $-NHCONHR^6$, $-CO_2R^{10}$, and $-C(O)N(R10)_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of $C_1$-$C_6$ alkyl, halo, $-OC(O)OR^6$, $-OC(O)R^6$, $-OR^{10}$, $-SR^{10}$, $-N(R^{10})_2$, $-C(O)R^{10}$, $-NO_2$, $-CN$, $-CF_3$, $-SO_2(C_1$-$C_6$ alkyl), $-S(O)(C_1$-$C_6$ alkyl), $-NR^{10}SO_2R^6$, $-SO_2N(R^6)_2$, $-NHCOOR^6$, $-NHCOR^6$, $-NHCONHR^6$, $-CO_2R^{10}$, and $-C(O)N(R^{10})_2$; and each $R^{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of $C_1$-$C_6$ alkyl, halo, $-OC(O)OR^6$, $-OC(O)R^6$, $-OR^{10}$, $-SR^{10}$, $-N(R^{10})_2$, $-C(O)R^{10}$, $-NO_2$, $-CN$, $-CF_3$, $-SO_2(C_1$-$C_6$ alkyl), $-S(O)(C_1$-$C_6$ alkyl), $-NR^{10}SO_2R^6$, $-SO_2N(R^6)_2$, $-NHCOOR^6$, $-NHCOR^6$, $-NHCONHR^6$, $-CO_2R^{10}$, and $-C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

\* \* \* \* \*